United States Patent
Wu et al.

(10) Patent No.: US 12,162,894 B2
(45) Date of Patent: Dec. 10, 2024

(54) STRUCTURAL ANALOG OF CYCLOTHEONELLAZOLE A, AND SYNTHETIC METHOD THEREFOR AND APPLICATION METHOD THEREOF

(71) Applicant: The Second People's Hospital of Shenzhen (Shenzhen Institute of Geriatrics), Shenzhen (CN)

(72) Inventors: Zhengzhi Wu, Shenzhen (CN); Bohua Long, Shenzhen (CN); Zhiyue Li, Shenzhen (CN); Liuyang Pu, Shenzhen (CN); Shengquan Hu, Shenzhen (CN); Limin Li, Shenzhen (CN)

(73) Assignee: The Second People's Hospital of Shenzhen (Shenzhen Institute of Geriatrics), Shenzhen (CN)

( * ) Notice: Subject to any disclaimer, the term of this patent is extended or adjusted under 35 U.S.C. 154(b) by 0 days.

(21) Appl. No.: 18/527,398

(22) Filed: Dec. 4, 2023

(65) Prior Publication Data
US 2024/0246998 A1     Jul. 25, 2024

(30) Foreign Application Priority Data
Dec. 5, 2022    (CN) .......................... 202211552246.0

(51) Int. Cl.
*C07D 513/04*    (2006.01)
*A61P 31/14*    (2006.01)

(52) U.S. Cl.
CPC ............ *C07D 513/04* (2013.01); *A61P 31/14* (2018.01)

(58) Field of Classification Search
CPC .................................................. C07D 513/04
USPC ........................................................ 514/367
See application file for complete search history.

(56) References Cited

FOREIGN PATENT DOCUMENTS

CN           116082436 A   *   5/2023   ............. A61K 38/07

* cited by examiner

*Primary Examiner* — Kahsay Habte

(57) ABSTRACT

A structural analog of Cyclotheonellazole A, and a synthetic method therefor and an application method thereof are provided. A compound with a structure of formula (I) and a pharmaceutically acceptable salt thereof are provided. The formula (I) is as follows:

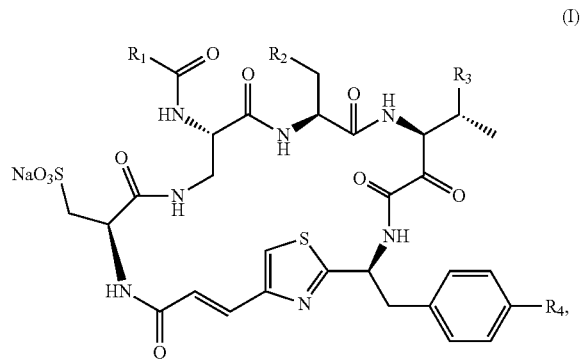

$R_1$, $R_2$, $R_3$ and $R_4$ are independently selected form the group consisting of H, a C1-C6 alkyl group, a C1-C6 alkoxy group, a halogen group, a hydroxyl group, an amino group, a nitro group, a cyano group, and a sulfydryl group. Based on the total synthetic route of Cyclotheonellazole A, the classical reverse synthesis analysis is utilized, the structural modification is purposefully carried out, a mother nucleus of the natural product remains unchanged, and the structural analog 1a is obtained by replacing a left side chain with a simple formylamine, thereby confirming the excellent protease inhibitory activity thereof, and having a strong application prospect in the pharmaceutical industry.

5 Claims, 2 Drawing Sheets

STRUCTURAL ANALOG OF CYCLOTHEONELLAZOLE A, AND SYNTHETIC METHOD THEREFOR AND APPLICATION METHOD THEREOF

TECHNICAL FIELD

The disclosure relates to the technical field of drugs, and more particularly to a structural analog of Cyclotheonellazole A, and a synthetic method therefor and an application method thereof.

BACKGROUND

Corona Virus Disease 2019 (Covid-19) caused by severe acute respiratory syndrome coronavirus 2 (SARS-CoV-2) has become a global epidemic that seriously threatens human life and health. Studies have shown that acute lung injury/acute respiratory distress syndrome (ALI/ARDS) caused by coronavirus is the main cause of poor prognosis and low survival rate of critically ill patients. Vaccines are considered the most effective method to block SARS-CoV-2 at present. However, a sensitivity of virus to vaccine-induced immunity is decreased with an emergence of the Covid-19 strain; therefore, developing drugs for SARS-CoV-2 is a top priority at present.

A specific path of SARS-CoV-2 virus infecting host cells is as follows: the SARS-CoV-2 virus are combined with receptor protein angiotensin converting enzyme 2 in the host cells, the SARS-CoV-2 virus are fused with host cell membrane under an action of transmembrane serine protease 2 (TMPRSS2), viral genome is released into cytoplasm of the host cells, and a transcriptional replication is further performed under an action of mainprotease (Mpro) of the SARS-CoV-2 virus to complete an assembly of progeny virus, to thereby release the progeny virus to outsides of the host cells.

Neutrophil elastase (NE) is a serine proteinase widely expressed in pancreas and neutrophils. Under a normal physiological condition, the NE can clear bacteria and damaged tissues, and promote tissue regeneration, however, under a pathological condition, overexpression of the NE can damage blood vessels, thus leading to inflammation, viral or bacterial infections. Studies have shown that, in a COVID-19 patient, the NE released by the neutrophils can activate epithelial sodium ion ($Na^+$) transporters, leading to hypertension and pulmonary airway dehydration, thus resulting in reduced mucociliary clearance efficiency, lung barrier dysfunction, and pro-inflammatory cytokine release, and ultimately leading to severe ALI/ARDS in the COVID-19 patient. Therefore, the Mpro and the NE are all considered as potential targets for a treatment of the SARS-CoV-2.

A Cyclotheonellazole A (CA) is a natural product of macrocyclic polypeptide isolated from sponge by Carmeli et al. of Tel Aviv University, Israel. Structurally, the CA is composed of 8 amino acids, 6 of which are non-proteinogenic amino acids and contain 7 chiral centers, and the structure of the CA is as follows:

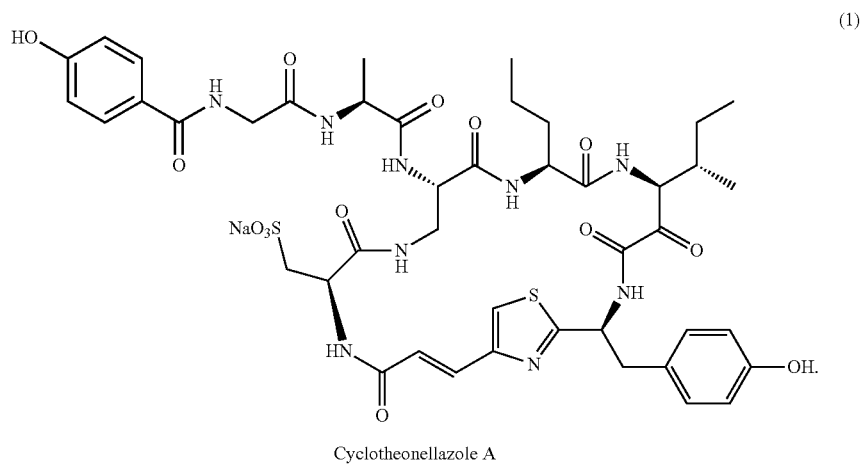

Cyclotheonellazole A

As the secondary metabolites of animals and plants, microorganisms and marine organisms, natural products have diversity and uniqueness in structure and biological activity. However, although the natural products are extremely active, it is unlikely to be directly used as medicines. Through systematic structure-activity relationship study of the CA, it is necessary to find a structural analog with simpler structure, high selectivity and good therapeutic window.

Due to a complexity of the structure of the CA, it has numerous stereoisomers, and biological activities between different stereoisomers often varies greatly. Research has found more natural stereoisomer products and confirmed their protease inhibitory activity, which is of great value for research of structure-activity relationships and reserve of candidate drugs for enzyme inhibitors.

SUMMARY

In order to solve problems in the related art, embodiments of the disclosure provide a structural analog of Cyclotheonellazole A, and a synthetic method therefor, and an application method thereof. Technical solutions are as follows.

According to a first aspect, an embodiment of the disclosure provides a compound or a pharmaceutically acceptable salt thereof, the compound having a structure represented by a general formula (I) expressed as follows:

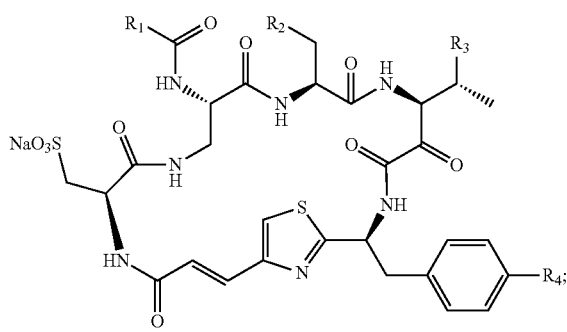

where $R_1$, $R_2$, $R_3$ and $R_4$ are independently selected form the group consisting of a hydrogen group (H), a C1-C6 alkyl group, a C1-C6 alkoxy group, a halogen group, a hydroxyl group, an amino group, a nitro group, a cyano group, and a sulfydryl group.

In an embodiment, the $R_1$ is H, the $R_2$ is a C1-C3 alkyl group, the $R_3$ is a C1-C3 alkyl group, and the $R_4$ is the hydroxyl group.

In an embodiment, the compound has a structure represented by a formula (1a) expressed as follows:

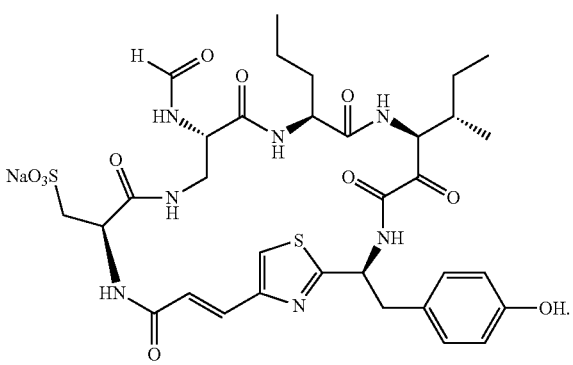

According to a second aspect, an embodiment of the disclosure provides a synthetic method of a structural analog of Cyclotheonellazole A, and the synthetic method includes:
removing a 9-fluorenylmethyloxycarbonyl (Fmoc) protection group from a compound 2 with diethanolamine (DEA) to obtain a first group-removed compound; performing a reaction on the first group-removed compound and ethyl formate ($C_3H_6O_2$) in a condition of seal tube and at a temperature of 80 degrees Celsius (° C.) to obtain formamide ($CH_3NO$); removing a tert-butyldiphenylsilyl (TBDPS) protection group from the formamide with ammonium fluoride ($NH_4F$) to obtain a second group-removed compound; activating a hydroxyl group of the second group-removed compound with methanesulfonyl chloride (MsCl) to obtain activated compound; performing a bimolecular nucleophilic substitution (SN2) reaction on the activated compound with potassium thioacetate (KSAc) to obtain a thioester; oxidizing the thioester with potassium monopersulphate triple salt (Oxone) to obtain a first sulfurous acid; removing a pivaloyl (Piv) group from the first sulfurous acid with triethylamine ($C_6H_{15}N$) in a reflux condition of methanol (MeOH) to obtain a secondary alcohol; oxidizing the secondary alcohol with 2-iodoxybenzoic acid (IBX) to obtain a α-keto-amide; oxidizing the α-ketoamide with selenium dioxide ($SeO_2$) to remove two allyl groups from the α-ketoamide, to thereby obtain a second sulfurous acid; and adding a saturated sodium chloride solution into the second sulfurous acid to obtain a compound 1a;

where a specific synthesis process of the compound 1a is as follows:

1) DEA, MeCN, rt
2) HCO$_2$Et, Seal tube, 80° C.
3) NH$_4$F, MeOH, reflux
4) MsCl, Et$_3$N, DCM, rt, 2 h
5) KSAc, DMF, rt, 2h
[2] →
6) Oxone (20 eq.), AcOH, AcOK, 65° C.
7) Et$_3$N/H$_2$O/MeOH, reflux, 2 d
8) IBX, DMSO, 50° C., 2 h
9) SeO$_2$, HOAc, dioxane, reflux
10) 1.0M NaCl, MeOH/H$_2$O, rt

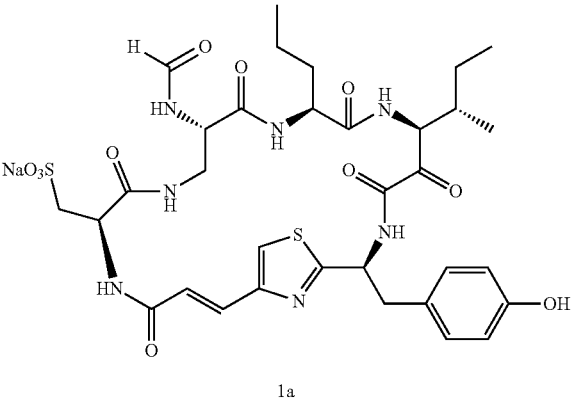

where a structure of the compound 2 is as follows:

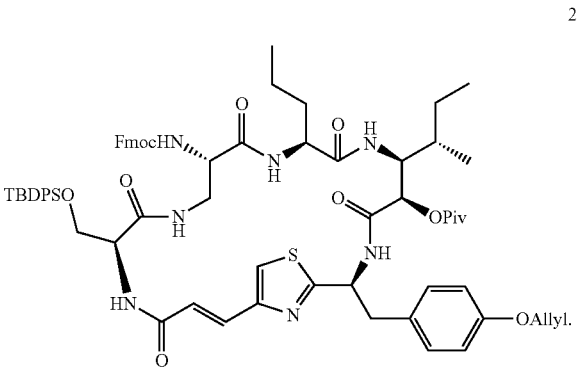

In an embodiment, a synthetic method of the compound 2 includes:
performing a condensation reaction on a compound 19 and a compound 20 to obtain a compound 21; protecting a primary alcohol group of the compound 21 with tert-butyldimethylsilyl chloride (TBSCL) to obtain a compound 22; performing a thionation reaction on the compound 22 with a Lawesson's reagent to obtain a compound 23; removing a t-butyldimethylsilyl (TBS) protection group from the compound 23 with the NH$_4$F to obtain a compound 24; performing a ring-closing reaction on the compound 24 with diethylaminosulfurtrifluoride (DAST) to obtain a ring-closed compound, oxidizing the ring-closed compound with 1,8-diazabicyclo[5.4.0]undec-7-ene (DBU) and bromotrichloro methane (CBrCl₃) to obtain a first oxidized compound, and adding an allyl group into the first oxidized compound to obtain a compound 25; reducing a methyl ester group of the compound 25 with lithium borohydride (BH₄Li) to obtain a reduced compound, oxidizing a primary alcohol group of the reduced compound with the IBX to obtain a second oxidized compound, and performing a Wittig reaction on the second oxidized compound to obtain a compound 26; and hydrolyzing an ethyl ester group of the compound 26 with sodium hydroxide (NaOH) to obtain a first hydrolyzed compound, and performing an esterification reaction on the first hydrolyzed compound and trichloroethanol (C₂H₃Cl₃O) to obtain a compound 27; where a specific synthesis process of the compound 27 is as follows:

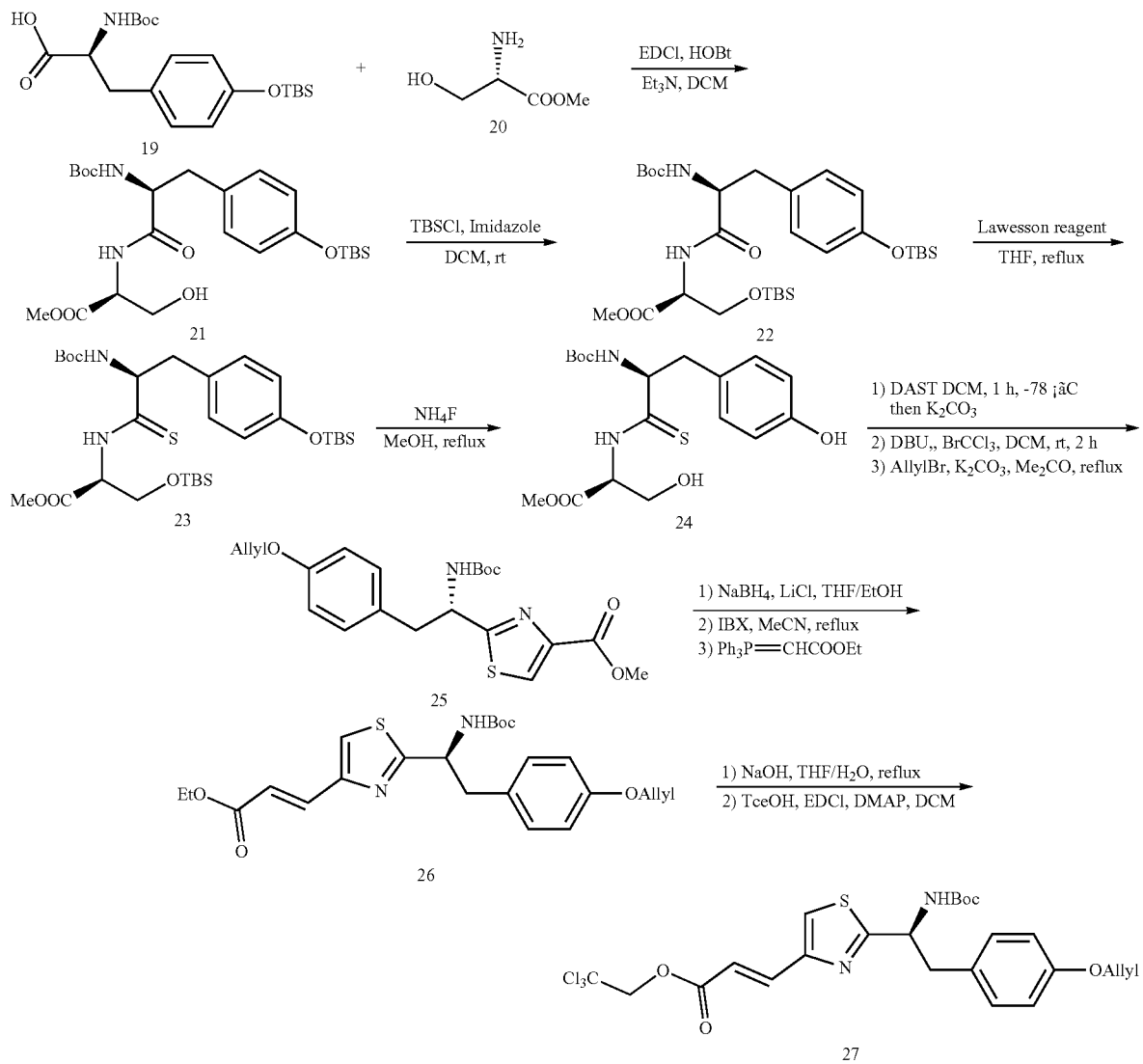

removing a Boc protection group from the compound 27 with trifluoroacetic acid to obtain a third group-removed compound, and performing a peptide grafting reaction on the third group-removed compound and a compound 18 to obtain a compound 28; and removing a Boc protection group from the compound 28 with the trifluoroacetic acid to obtain a fourth group-removed compound, and performing a peptide grafting reaction on the fourth group-removed compound and a compound 11 to obtain a compound 29;

where a specific synthesis process thereof is as follows:

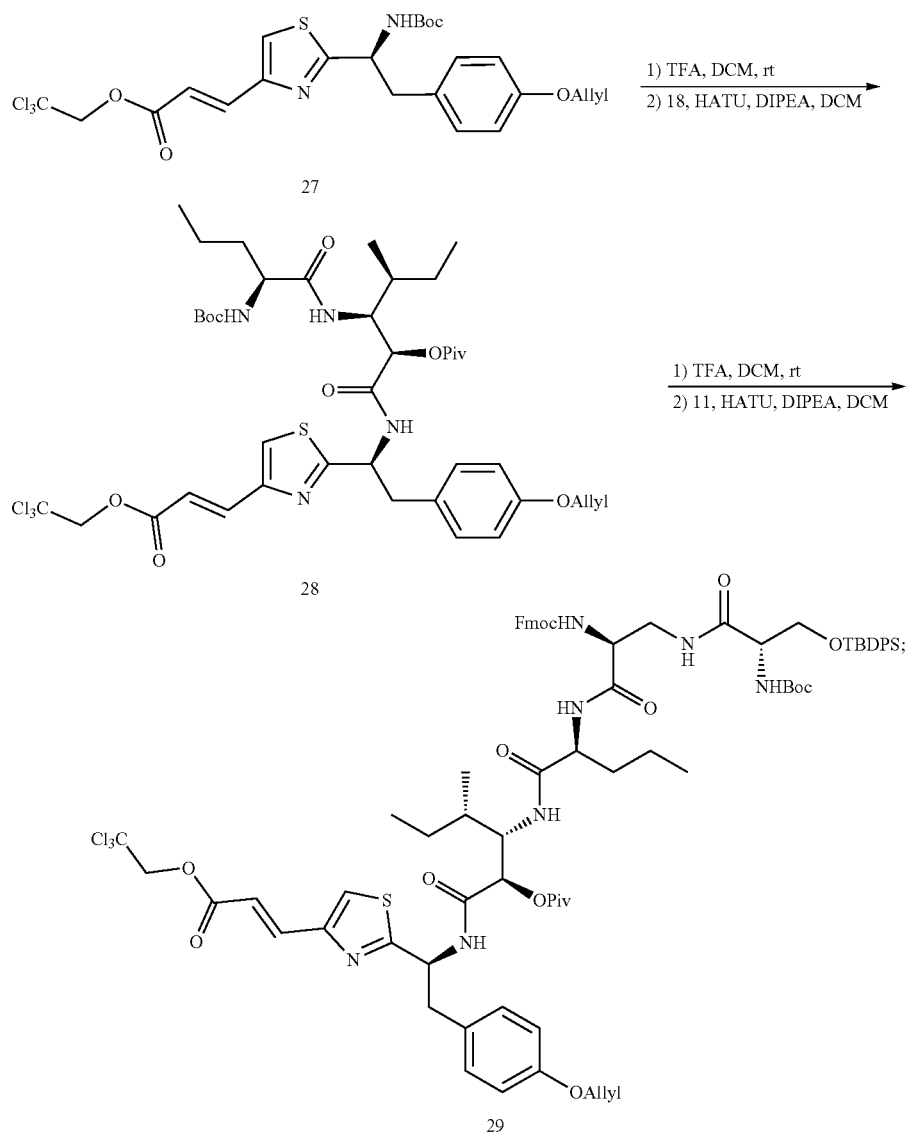

hydrolyzing a trichloroethyl ester group of the compound 29 in an acetic acid solution with a zinc dust to obtain a second hydrolyzed compound, removing a Boc protection group from the second hydrolyzed compound with the trifluoroacetic acid to obtain a fifth group-removed compound, and performing an intra-molecular macrocyclic-closing reaction on the fifth group-removed compound in a dichloromethane (DCM) solution with 2-(7-azabenzotriazol-1-yl)-N,N,N',N'-tetramethyluronium hexafluorophosphate (HATU) to obtain the compound 2;

where a specific synthesis process of the compound 2 is as follows:

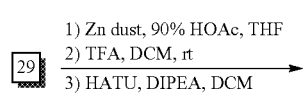

and
where structures of the compound 11 and the compound 18 are as follows:

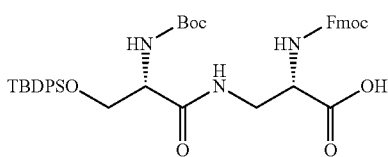

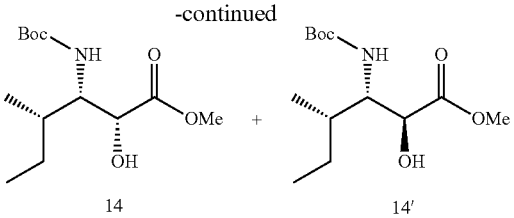

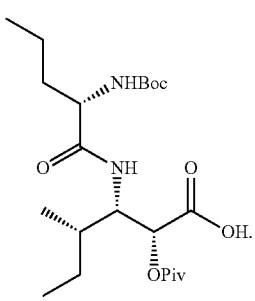

In an embodiment, a synthetic method of the compound 18 includes:

taking a compound 12 as a starting material, performing a methyl esterification on the compound 12 to obtain a methyl esterified compound, protecting an amino group of the methyl esterified compound with di-tert-butyl dicarbonate to obtain a first intermediate compound, and reducing a methyl ester group of the first intermediate compound with the lithium borohydride to obtain a compound 13; oxidizing a primary alcohol group of the compound 13 with the IBX to obtain an aldehyde, performing a reaction on the aldehyde and acetone cyanohydrin to obtain a second intermediate compound, refluxing and hydrolyzing, by using a MeOH solution of hydrogen chloride, the second intermediate compound without purifying to obtain a third hydrolyzed compound, and protecting an amino group of the third hydrolyzed compound with the di-tert-butyl dicarbonate to obtain two diastereoisomers, a compound 14 and a compound 14';

where a specific synthesis process of the compound 14 and the compound 14' is as follows:

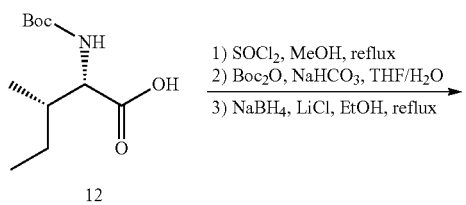

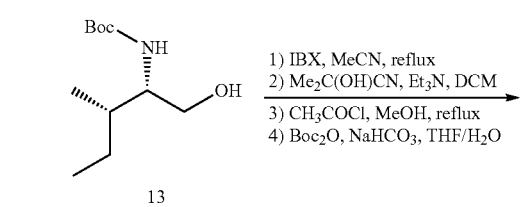

performing a reaction on the compound 14 and pivaloyl chloride ($C_5H_9ClO$) to obtain a compound 15, removing a Boc protection group of the compound 15 with the trifluoroacetic acid to obtain a sixth group-removed compound, and preforming a peptide grafting reaction on the sixth group-removed compound and a compound 16 to obtain a compound 17; and hydrolyzing a methyl ester group of the compound 17 in a reflux condition of pyridine with lithium iodide to obtain the compound 18;

where a specific synthesis process of the compound 18 is as follows:

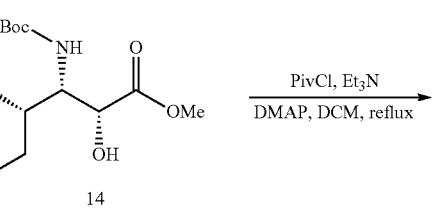

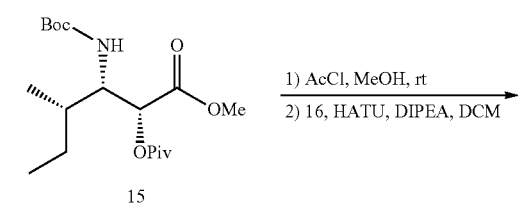

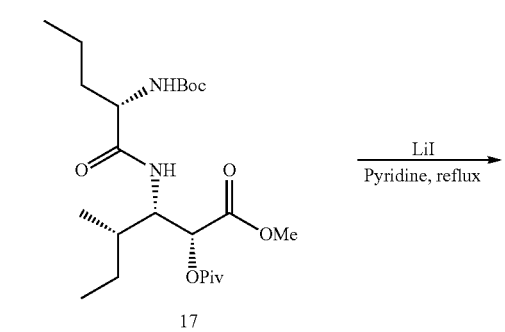

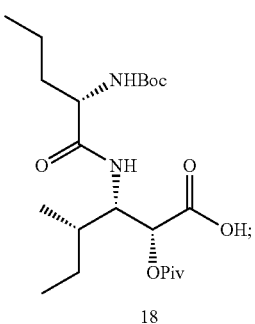

and
where a structure of the compound 16 is as follows:

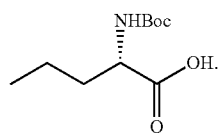

In an embodiment, a synthetic method of the compound 11 includes:
removing a Boc protection group of a compound 8 with the trifluoroacetic acid to obtain a seventh group-removed compound, and preforming a peptide grafting reaction on the seventh group-removed compound and a compound 9 to obtain a compound 10; and removing a phenoxyacetyl (Pac) protection group from the compound 10 in the acetic acid solution with the zinc dust to obtain the compound 11;
where a specific synthesis process of the compound 11 is as follows:

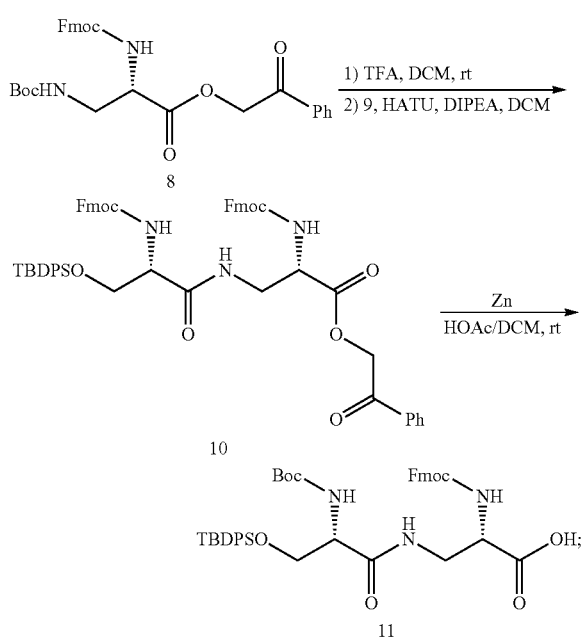

and
where a structure of the compound 9 is as follows:

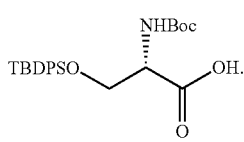

In an embodiment, a synthetic method of the compound 8 includes:
taking a compound 6 as a starting material, protecting an amino group of the compound 6 with N-(9-fluorenyl-methoxycarbonyloxy)succinimide (Fmoc-Osu) to obtain a compound 7, and performing a Hofmann rearrangement reaction on the compound 7 to obtain a compound 3; and protecting an amino group of the compound 3 with the di-tert-butyl dicarbonate ($BOC_2O$), and protecting a carboxyl group of the compound 3 with phenacyl bromide (PacBr), to obtain the compound 8;
where a specific synthesis process of the compound 8 is as follows:

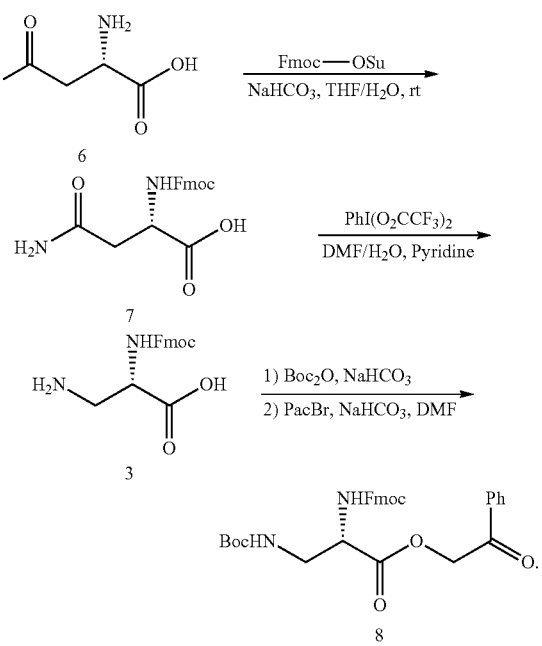

According to a third aspect, an embodiment of the disclosure provides a pharmaceutical composition, and the pharmaceutical composition includes anyone of the compounds and the pharmaceutically acceptable salts thereof as described in the first aspect.

According to a fourth aspect, an embodiment of the disclosure provides an application method of anyone of the compounds and the pharmaceutically acceptable salts thereof as described in the first aspect, and the application method includes: applying the compound and the pharmaceutically acceptable salt thereof to prepare a protease inhibitor.

The technical solutions provided by the embodiments of the disclosure at least has the following beneficial effects. Based on the total synthetic route of Cyclotheonellazole A, the structural modification is purposefully carried out by using the classical inverse synthetic analysis, so that a mother nucleus of the natural product remains unchanged, and a structural analog 1a (TM) is obtained by replacing a left side chain with simple formamide, which confirms the excellent protease inhibitory activity of the structural analog of Cyclotheonellazole A and has a strong application prospect in the pharmaceutical industry.

BRIEF DESCRIPTION OF DRAWINGS

In order to provide a clearer explanation of technical solutions in embodiments of the disclosure, drawings required in descriptions of the embodiments will be simply introduced below. Apparently, the drawings described below are merely some of the embodiments of the disclosure, for those skilled in the art; other drawings can be obtained according to the drawings without creative work.

DETAILED DESCRIPTION OF EMBODIMENTS

Figure 1:
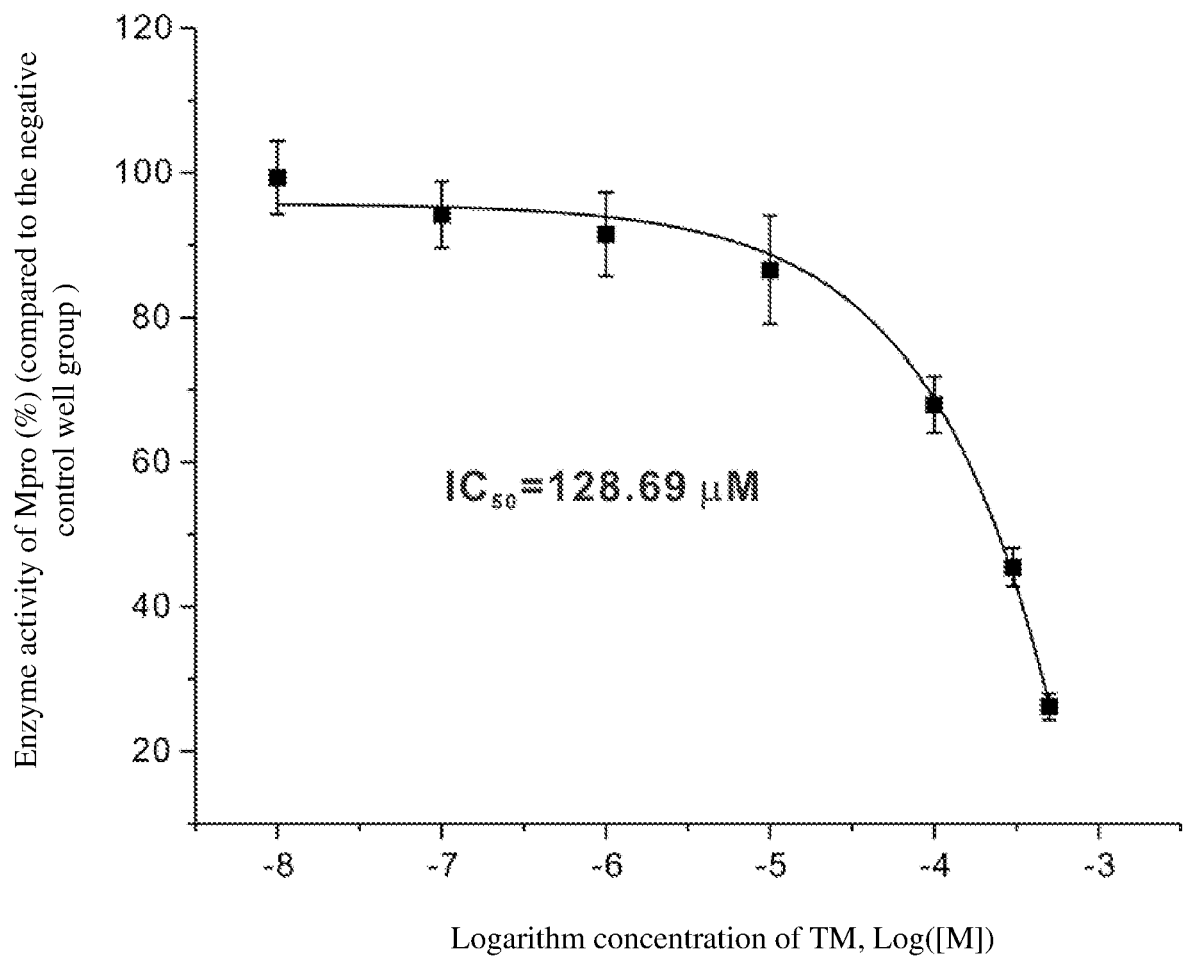
FIG. 1 illustrates a schematic diagram of an enzyme activity of main protease (Mpro) of SARS-CoV-2 virus under the inhibiting of the TM according to an embodiment of the disclosure.

In order to make purposes, technical solutions and advantages of the disclosure more clearly, embodiments of the disclosure will be further described in conjunction with drawings.

A Synthesis of a Compound 1a

A retrosynthesis analysis of the compound 1a is as follows:

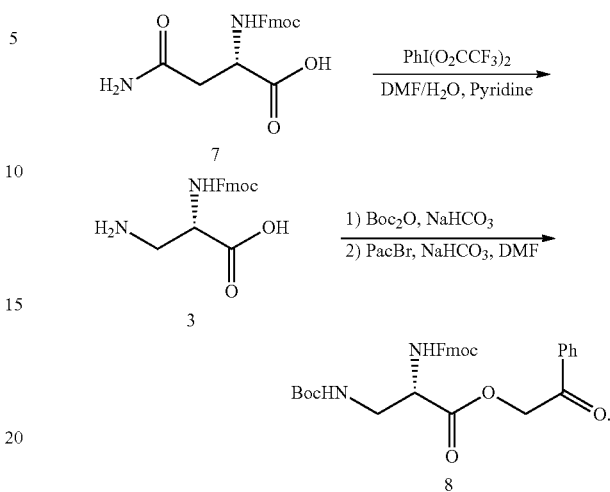

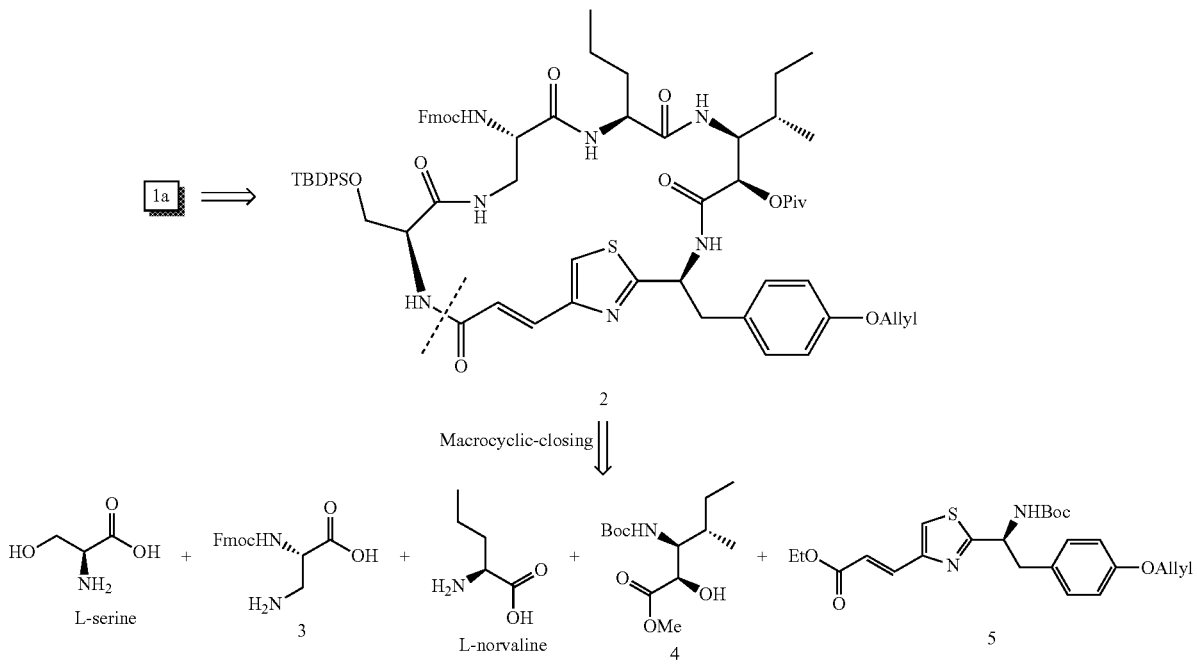

(1) A synthesis process of a compound 8 is as follows:

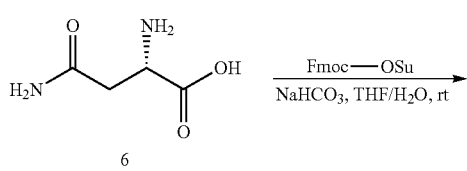

L-asparagine (i.e., a compound 6) (20 grams abbreviated as g, 151.4 micromolar abbreviated as mmol) is dissolved in a mixed solvent of tetrahydrofuran (THF)/water (H$_2$O) (1:1, 1000 millimeters abbreviated as mL), sodium bicarbonate (NaHCO$_3$) solid (33.6 g, 400 mmol) is added, and after stirring evenly, N-(9-fluorenylmethoxycarbonyloxy)succinimide (Fmoc-Osu) (51.0 g, 151.4 mmol) is added to thereby obtain a mixture. After stirring of the mixture for reacting at a room temperature for 15 hours (h), the mixture is diluted by adding water (1000 mL) to obtain a diluted mixture. Hydrochloric acid is added to acidify the diluted mixture to make a potential of hydrogen (pH) thereof be equal to 2, and a large amount of white solids are precipitated. The white solids are filtered to obtain a filter residue, the filter residue is washed by a large amount of water (2000 mL) to obtain solids, and the solids are dried in an oven to obtain a compound 7.

The compound 7 is dissolved in a mixed solvent of N,N-dimethylformamide (DMF)/H₂O (2:1, 600 mL), after cooling to a temperature of 0 Celsius degree (° C.), [bis(trifluoroacetoxy)iodo]benzene (PhI(O₂CCF₃)₂) (72.0 g, 166.5 mmol) is added, and after stirring for 15 minutes (min), pyridine (24.5 mL, 303 mmol) is added to obtain a mixture. After 30 min, the mixture is stirred for reacting at the room temperature for 15 h to obtain a reacted mixture. The reacted mixture is concentrated under reduced pressure to remove all solvents therein, diluted by adding water (500 mL), and acidified to pH=2 by adding hydrochloric acid to thereby obtain an aqueous phase. The aqueous phase is washed for twice with ethyl acetate (EA) (200 mL) to obtain washed aqueous phase (i.e., a compound 3).

NaHCO₃ solid is slowly added into the washed aqueous phase (i.e., the compound 3) to neutralize the compound 3 to make pH=8, and THF (500 mL) and di-tert-butyl dicarbonate (Boc₂o) (34.5 mL, 151.0 mmol) are added to obtain a mixture. After stirring of the mixture for reacting at the room temperature for 10 h, the mixture is concentrated under reduced pressure to remove THF, acidified to make pH=4 by adding hydrochloric acid, and extracted for three times with EA (500 mL) to obtain organic phases. The organic phases are merged, dried with anhydrous sodium sulfate (Na₂SO₄), and concentrated under reduced pressure to obtain an intermediate.

The intermediate is dissolved in DMF (150 mL), and NaHCO₃ solid (33.6 g, 400 mmol) and 2-bromoacetophenone (PacBr) (30.0 g, 150 mmol) are added to obtain a mixture. After stirring of the mixture for reacting at the room temperature for 8 h, the mixture is concentrated under reduced pressure to remove solvents, diluted by adding water (500 mL) and extracted for twice with EA (500 mL) to obtain organic phases. The organic phases are merged, dried with anhydrous Na₂SO₄, and concentrated under reduced pressure to obtain a crude product. Petroleum ether (PE) and EA with a ratio of 2:1 are used as an eluent to perform a flash column chromatography on the crude product to obtain the compound 8 (a white solid, 66.0 g), a total yield is 80% through the above four steps.

The compound 8 is detected through hydrogen-1 nuclear magnetic resonance ($^1$H NMR), carbon-13 nuclear magnetic resonance ($^{13}$C NMR) and high-resolution mass spectrometry (HRMS), the compound 8 is a pure compound, and performance indicators or characterization data of the compound 8 are as follows: $[\alpha]^2D^5$-70.2 (c0.82, CHCl₃); $^1$H NMR (400 MHZ, CDCl₃): δ 7.90 (d, J=7.7 Hz, 2H), 7.74 (d, J=7.5 Hz, 2H), 7.61 (d, J=6.0 Hz, 3H), 7.49 (t, J=7.6 Hz, 2H), 7.38 (t, J=7.4 Hz, 2H), 7.28 (dd, J=12.9, 5.8 Hz, 2H), 6.36 (s, 1H), 5.82 (s, 1H), 5.67 (d, J=16.5 Hz, 1H), 5.24 (d, J=16.5 Hz, 1H), 4.64-4.49 (m, 1H), 4.34 (dd, J=15.1, 8.6 Hz, 2H), 4.24 (t, J=7.1 Hz, 1H), 3.89 (s, 1H), 3.68 (d, J=14.1 Hz, 1H), 1.48 (s, 9H); $^{13}$C NMR (100 MHz, CDCl₃): δ 192.17, 170.01, 157.23, 156.06, 143.79, 141.12, 134.20, 133.57, 128.87, 127.72, 127.55, 126.96, 125.16, 119.80, 79.89, 67.13, 66.52, 55.49, 46.97, 42.17, 28.21; HR-ESIMS m/z: calculated for C₃₁H₃₂N₂O₇Na⁺ [M+Na]⁺: 567.2210, found 567.2214.

(2) A synthesis process of a compound 11 is as follows:

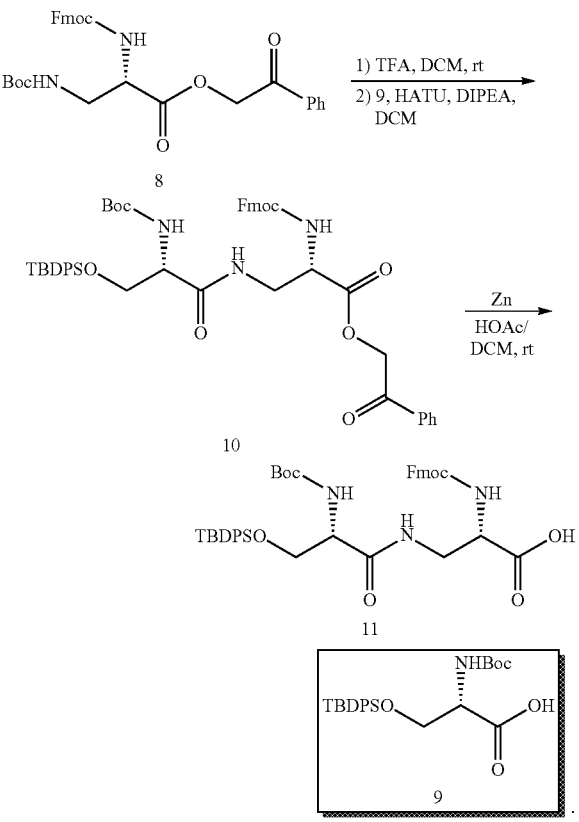

The compound 8 (23.4 g, 9 mmol) is dissolved in dichloromethane (DCM) solution (200 mL), and trifluoroacetic acid (TFA) (40 mL) is added to obtain a mixture. After stirring of the mixture for reacting at the room temperature for 2 h, the mixture is concentrated under reduced pressure and dried fully to obtain an intermediate amine.

The intermediate amine is dissolved in anhydrous DCM (500 mL), and 2-(7-azabenzotriazol-1-yl)-N,N,N',N'-tetramethyluronium hexafluorophosphate (HATU) (20.0 g, 52 mmol) and a compound 9 (18.6 g, 42 mmol) are sequentially added. After cooling to the temperature of 0° C., N,N-diisopropylethylamine (DIPEA) (21.5 mL, 128.7 mmol) is slowly added dropwise to react for 30 min to obtain a mixture. After heating of the mixture to the room temperature for reacting for 12 h, an organic phase is obtained, and the organic phase is sequentially washed by diluted hydrochloric acid (300 mL) with a concentration of 2 molar per liter (M), washed by saturated NaHCO₃ solution (300 mL) to thereby obtain a washed organic phase. The washed organic phase is dried with anhydrous Na₂SO₄, concentrated under reduced pressure to obtain a crude product. PE and EA with a ratio of 2:1 are used as an eluent to perform a flash column chromatography on the crude product to obtain a compound 10 (a white solid, 31.0 g), a total yield thereof is 85%.

The compound 10 is detected through $^1$H NMR, $^{13}$C NMR and HRMS, the compound 10 is a pure compound, and performance indicators or characterization data of the compound 10 are as follows: $[\alpha]^2D^5$-18.2 (c1.0, CHCl₃); $^1$H NMR (400 MHZ, CHCl₃): δ 7.92 (d, J=7.2 Hz, 2H), 7.74 (d, J=7.3 Hz, 2H), 7.63 (t, J=6.2 Hz, 7H), 7.51 (t, J=7.7 Hz, 2H), 7.43-7.30 (m, 10H), 6.16 (d, J=6.8 Hz, 1H), 5.68 (d, J=16.5 Hz, 1H), 5.57 (s, 1H), 5.27 (d, J=16.4 Hz, 1H), 4.69 (s, 1H), 4.31 (s, 3H), 4.23 (d, J=7.4 Hz, 1H), 4.13-4.10 (m, 1H), 3.93-3.83 (m, 1H), 3.72 (d, J=13.8 Hz, 1H), 1.35 (s, 9H), 1.04 (s, 9H); $^{13}C$ NMR (100 MHz, $CHCl_3$): δ 192.29, 171.74, 169.74, 156.14, 155.56, 143.85, 141.16, 135.52, 135.46, 134.78, 134.51, 133.39, 132.96, 132.60, 129.83, 129.42, 128.97, 127.94, 127.76, 127.56, 127.08, 127.04, 125.37, 119.79, 79.99, 67.39, 66.62, 64.13, 60.33, 56.97, 54.59, 47.01, 41.05, 28.19, 26.70, 26.53, 19.23; HR-ESIMS m/z: calculated for $C_{50}H_{55}N_3O_9SiNa^+$ $[M+Na]^+$: 892.3708, found 892.3710.

The compound 10 (31.0 g, 35.6 mmol) is dissolved in DCM solution (500 mL), acetic acid solution (100 mL) is added, and after stirring evenly, zinc dust (46.3 g, 712 mmol) is added to obtain a mixture. After stirring of the mixture for reacting at the room temperature for 5 h, the mixture is concentrated under reduced pressure to remove DCM, and diluted by adding the water (800 mL) to obtain a diluted mixture. $NaHCO_3$ solid is slowly added to neutralize the diluted mixture to pH=8 to thereby obtain a neutralized mixture. The neutralized mixture is extracted with DCM solution (800 mL) and filtered to remove the zinc dust to obtain a filtrate. The filtrate is separated into an organic phase and an aqueous phase. The aqueous phase is extracted for twice with DCM solution (500 mL) to obtain organic phases. The organic phases are merged, dried with anhydrous $Na_2SO_4$, and concentrated under reduced pressure to obtain the compound 11.

(3) A synthesis process of a compound 14 and a compound 14' is as follows:

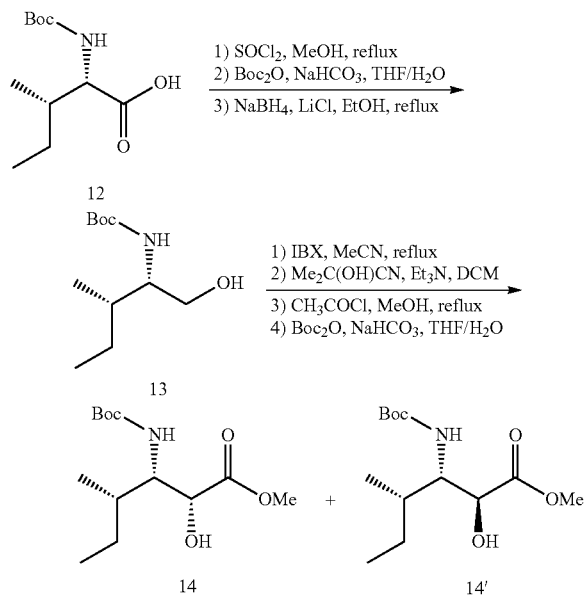

L-isoleucine (i.e., a compound 12) (20.0 g, 160.0 mmol) is dissolved in methanol solution (MeOH) (200 mL), and after cooling to the temperature of 0° C., thionyl chloride ($SOCl_2$) (23 mL, 320 mmol) is slowly added dropwise to react for 30 min to obtain a mixture. After heating and refluxing of the mixture for reacting for 1 h, the mixture is cooled to the room temperature, and the mixture is concentrated under reduced pressure to obtain a first intermediate.

The first intermediate obtained in the previous step is dissolved in a mixed solvent of $THF/H_2O$ (1:1, 1000 mL), $NaHCO_3$ solid (40.3 g, 480 mmol) is added, and after stirring evenly, $Boc_2O$ (36.8 mL, 160.0 mmol) is added to obtain a mixture. After stirring of the mixture for reacting for 15 h, the mixture is concentrated under reduced pressure to remove THF thereof, diluted by adding water (200 mL), and extracted for three time with EA (500 mL) to obtain organic phases. The organic phases are merged, dried with anhydrous $Na_2SO_4$, and concentrated under reduced pressure to obtain a second intermediate.

The second intermediate obtained in the previous step is dissolved in ethanol (EtOH) (1000 mL), and a sodium borohydride ($NaBH_4$) solid (12.2 g, 320 mmol) and a lithium chloride (LiCl) (13.6 g, 320 mmol) are sequentially added to obtain a mixture. After heating and refluxing of the mixture for reacting for 3 h, the mixture is cooled to the room temperature, and the mixture is concentrated under reduced pressure to remove the ethanol, to thereby obtain a solid. Water (800 mL) is added to dissolve the solid to obtain a solution. Hydrochloric acid is slowly added dropwise into the solution to make pH=5 to obtain an acidic solution. The acidic solution is extracted for three times by using EA (500 mL) to thereby obtain organic phases. The organic phases are merged, dried with anhydrous $Na_2SO_4$, and concentrated under reduced pressure to obtain a compound 13 (31.3 g), and a total yield thereof is 90% through the above three steps.

The compound 13 (31.3 g, 144 mmol) is dissolved in acetonitrile (300 mL), and 2-iodoxybenzoic acid (IBX) (44.8 g, 160 mmol) is added to obtain a mixture. After heating and refluxing of the mixture for reacting for 2 h, the mixture is cooled to the room temperature, and the mixture is filtered to obtain a filter residue and a filtrate. The filter residue is washed for once with acetonitrile (200 mL), and the filtrate is concentrated under reduced pressure to obtain an intermediate aldehyde.

The intermediate aldehyde obtained in the previous step is dissolved in DCM (300 mL), and triethylamine ($Et_3N$) (24.0 mL, 173 mmol) and acetone cyanohydrin (14.6 mL, 160 mmol) are added to obtain a mixture. After stirring of the mixture for reacting at the room temperature for 2 h, and the mixture is filtered to obtain a filtrate. The filtrate is concentrated under reduced pressure to obtain an intermediate cyanohydrin.

The intermediate cyanohydrin obtained in the previous step is dissolved in MeOH (300 mL), and after cooling to the temperature of 0° C., acetyl chloride (51.0 mL, 720 mmol) is slowly added dropwise for reacting for 30 min to obtain a mixture. After heating and refluxing of the mixture for reacting for 10 h, the mixture is cooled to the room temperature, and the mixture is concentrated under reduced pressure to obtain a third intermediate.

The third intermediate obtained in the previous step is dissolved in mixed solvent of the $THF/H_2O$ (1:1, 1000 mL), $NaHCO_3$ solid (40.3 g, 480 mmol) is added, after stirring evenly, $Boc_2O$ (33.0 mL, 144 mmol) is added to obtain a mixture. After stirring of the mixed solution for reacting at the room temperature for 10 h, the mixture is concentrated under reduced pressure to remove THF therein, diluted by adding water (200 mL), and extracted for three times with EA (500 mL) to obtain organic phases. The organic phases are merged, dried with anhydrous $Na_2SO_4$, and concentrated under reduced pressure to obtain a crude product. PE and EA with a ratio of 5:1 are used as an eluent to perform a flash column chromatography on the crude product to obtain the compound 14 (16.8 g) and the compound 14' (16.8 g), a total yield thereof is 85%.

The compound 14 is detected through $^1$H NMR, $^{13}$C NMR and HRMS, the compound 14 is a pure compound, and performance indicators or characterization data of the compound 14 are as follows: $[\alpha]^2D^5$-48.6 (c1.41, CHCl$_3$); $^1$H NMR (400 MHZ, CHCl$_3$): δ 4.83 (d, J=9.0 Hz, 1H), 4.36 (s, 1H), 3.77 (s, 3H), 3.32 (s, 1H), 1.62 (dd, J=15.3, 7.1 Hz, 1H), 1.40 (s, 9H), 1.34-1.03 (m, 2H), 0.99 (d, J=6.5 Hz, 3H), 0.90 (t, J=7.4 Hz, 3H); $^{13}$C NMR (100 MHz, CHCl$_3$): δ 174.87, 155.46, 79.25, 70.28, 56.96, 52.66, 36.18, 28.19, 25.52, 15.66, 10.92; HR-ESIMS m/z: calculated for C$_{13}$H$_{25}$NO$_5$Na$^+$ [M+Na]$^+$: 298.1733, found 298.1735.

The compound 14' is detected through $^1$H NMR, $^{13}$C NMR and HRMS, the compound 14' is a pure compound, and performance indicators or characterization data of the compound 14' are as follows: $[\alpha]^2D^5$-8.1 (c0.62, CHCl$_3$); $^1$H NMR (400MHZ, CHCl$_3$): δ 4.79 (d, J=8.7 Hz, 1H), 4.31 (m, 1H), 3.79 (s, 3H), 3.37 (s, 1H), 1.64-1.60 (m, 1H), 1.45 (d, J=3.9 Hz, 9H), 1.21-1.05 (m, 2H), 0.93-0.87 (m, 6H); $^{13}$C NMR (100 MHz, CHCl$_3$): δ 173.85, 156.18, 79.68, 72.59, 58.01, 52.49, 35.37, 28.30, 28.19, 24.84, 15.94, 11.13; HR-ESIMS m/z: calculated for C$_{13}$H$_{25}$NO$_5$Na$^+$ [M+Na]$_+$: 298.1733, found 298.1735.

(4) A synthesis process of a compound 18 is as follows:

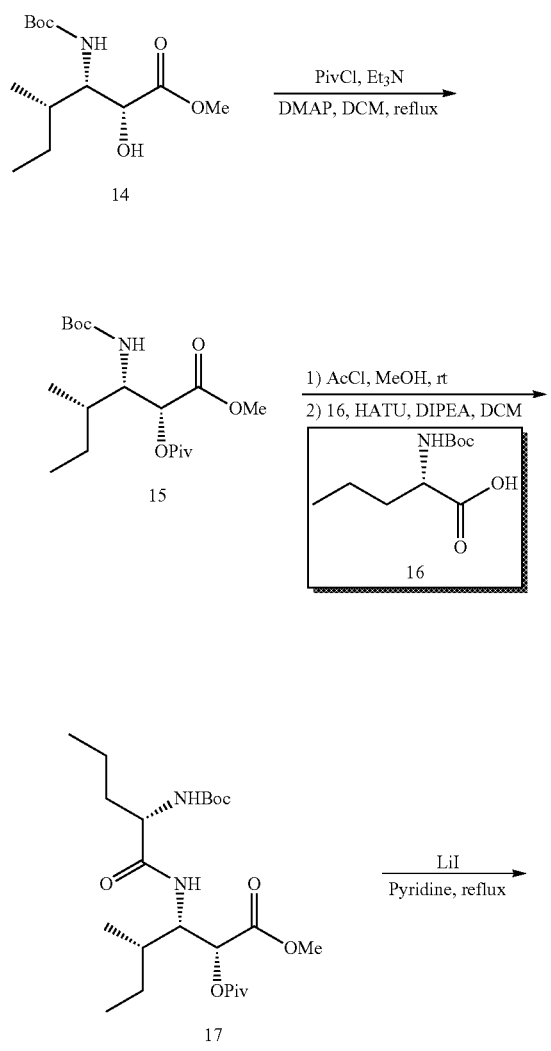

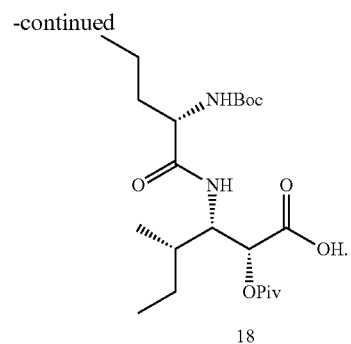

The compound 14 (16.8 g, 61.2 mmol) is dissolved in anhydrous DCM (200 mL), Et$_3$N (12.8 mL, 92.0 mmol) and 4-dimethylaminopyridine (DMAP) (0.75 g, 6.1 mmol) are added, and after cooling to the temperature of 0° C., pivaloyl chloride (8.3 mL, 67.5 mmol) is slowly added dropwise to react for 30 min to obtain a mixture. After heating and refluxing of the mixture for reacting for 3 h, the mixture is cooled to the room temperature, and the mixture is concentrated under reduced pressure to remove DCM therein to obtain a residue. The residue is dissolved in EA (500 mL) to obtain a residue solution. The residue solution is sequentially washed by diluted hydrochloric acid (150 mL) with a concentration of 1 M, washed by saturated NaHCO$_3$ solution (200 mL), dried with anhydrous Na$_2$SO$_4$, and concentrated under reduced pressure to obtain a compound 15.

The compound 15 obtained in the previous step is dissolved in MeOH solution (150 mL), and after cooling to the temperature of 0° C., acetyl chloride (21.8 mL, 306 mmol) is slowly added dropwise to react for 30 min to obtain a mixture. After heating of the mixture to the room temperature for reacting for 2 h, the mixture is concentrated under reduced pressure to obtain an intermediate.

The intermediate obtained in the previous step is dissolved in anhydrous DCM (400 mL), HATU (30.4 g, 80 mmol) and a compound 16 (13.0 g, 60 mmol) are sequentially added, and after cooling to a temperature of 0° C., DIPEA (30.0 mL, 180 mmol) is slowly added dropwise for reacting for 30 min to obtain a mixture. After heating of the mixture to the room temperature for reacting for 12 h, an organic phase is obtained. The organic phase is sequentially washed by diluted hydrochloric acid (300 mL) with a concentration of 2 M, washed by using saturated NaHCO$_3$ solution (300 mL), dried with anhydrous Na$_2$SO$_4$, and concentrated under reduced pressure to obtain a crude product. PE and EA with a ratio of 2:1 is used as an eluent to perform a flash column chromatography on the crude product to obtain a compound 17 (23.4 g), and a total yield thereof is 85% through the above three steps.

The compound 17 is detected through $^1$H NMR, $^{13}$C NMR and HRMS, the compound 17 is a pure compound, and performance indicators or characterization data of the compound 17 are as follows: $[\alpha]^2D^5$-50.7 (c0.67, CHCl$_3$); $^1$H NMR (400 MHZ, CHCl$_3$): δ 6.31 (d, J=9.7 Hz, 1H), 5.15 (d, J=2.0 Hz, 1H), 5.07 (dd, J=15.5, 6.3 Hz, 1H), 4.35-4.29 (m, 1H), 4.02-3.96 (m, 1H), 3.67 (s, 3H), 1.74 (d, J=7.1 Hz, 1H), 1.52-1.46 (m, 4H), 1.41 (s, 9H), 1.32 (d, J=7.4 Hz, 4H), 1.26 (s, 9H), 1.16 (s, 2H), 0.92-0.87 (m, 9H); $^{13}$C NMR (100 MHz, CHCl$_3$): δ 177.27, 171.94, 168.80, 155.86, 79.98, 71.37, 54.27, 53.48, 52.30, 38.83, 36.53, 28.21, 27.09, 26.96, 25.35, 18.71, 15.30, 13.63, 10.80; HR-ESIMS m/z: calculated for C$_{23}$H$_{42}$N$_2$O$_7$Na$^+$ [M+Na]$^+$: 480.2992, found 480.2994.

The compound 17 (23.4 g, 51 mmol) is dissolved in anhydrous pyridine (200 mL), and anhydrous lithium iodide (13.7 g, 102 mmol) is added to obtain a mixture. After heating and refluxing of the mixture for reacting for 8 h, the mixture is concentrated under reduced pressure to remove pyridine therein, diluted by adding water (500 mL), acidified by adding concentration hydrochloric acid to make pH=4, and extracted for three times with EA (400 mL) to obtain organic phases. The organic phases are merged, dried with anhydrous Na$_2$SO$_4$, and concentrated under reduced pressure to obtain a compound 18, and a crude yield thereof is 100%.

(5) A synthesis process of a compound 21 is as follows:

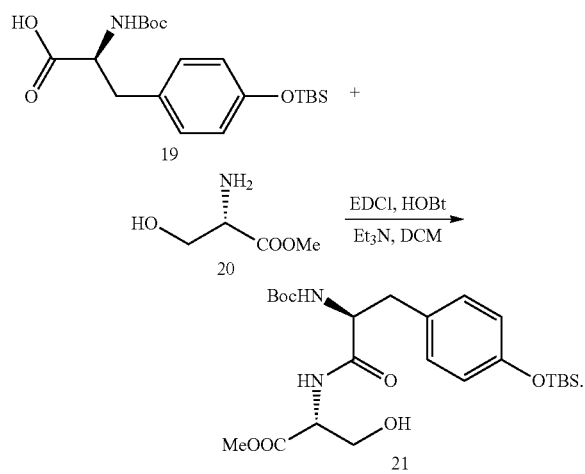

A compound 19 (23.3 g, 82.8 mmol) and a compound 20 (15.5 g, 99.4 mmol, 1.2 equivalent abbreviated as eq.) are mixed, the DCM solution (200 mL) is added therein, and then the Et$_3$N (45.8 mL, 331.2 mmol, 4.0 eq.), 1-ethyl-3(3-dimethylpropylamine) carbodiimide (EDCI) (20.6 g, 107.6 mmol, 1.3 eq.), and 1-hydroxybenzotriazole (HOBT) (5.6 g, 41.4 mmol, 0.5 eq.) are slowly added therein to obtain a mixture. After reacting of the mixture at the room temperature for 24 h, the mixture is washed by adding water (200 mL), and separated to obtain an organic phase. The organic phase is concentrated to obtain a crude product. The crude product is dissolved in EA (200 mL) to obtain a crude product solution. The crude product solution is washed by hydrochloric acid with a concentration of 2 normality (N), i.e., 2 mol/L, to thereby obtain an organic phase. The organic phase is washed by saturated salt water, dried with anhydrous Na$_2$SO$_4$, filtered, and concentrated to obtain the compound 21 (27.2 g, a yield of 86%).

The compound 21 is detected through $^1$H NMR, $^{13}$C NMR and HRMS, the compound 21 is a pure compound, and performance indicators or characterization data of the compound 21 are as follows: $^1$H NMR (400 MHZ, CHCl$_3$): δ 7.50 (s, 1H), 6.98 (dt, J=7.6, 1.1 Hz, 2H), 6.80 (t, J=5.5 Hz, 1H), 6.77-6.72 (m, 2H), 6.24 (s, 1H), 4.95 (t, J=7.1 Hz, 1H), 4.64-4.56 (m, 2H), 4.30 (t, J=6.9 Hz, 1H), 4.16 (ddd, J=12.4, 7.0, 5.4 Hz, 1H), 3.63 (s, 3H), 3.32 (ddt, J=12.5, 7.2, 1.1 Hz, 1H), 3.01 (ddt, J=12.5, 7.2, 1.1 Hz, 1H), 1.44 (s, 9H); $^{13}$C NMR (101 MHz, CHCl$_3$): δ 172.52, 171.89, 156.33, 155.69, 130.58, 128.85, 115.82, 79.69, 62.47, 56.85, 55.27, 53.19, 37.95, 28.34; HRMS (m/z): calculated for C$_{18}$H$_{26}$N$_2$NaO$_7$$^+$ ([M+Na]$^+$): 405.1632, found 405.1622.

(6) A synthesis process of a compound 22 is as follows:

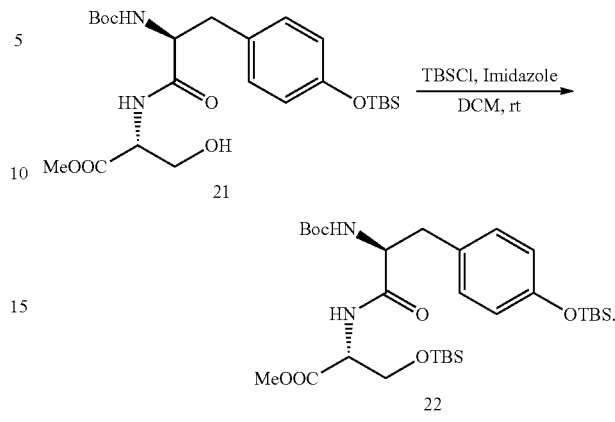

The compound 21 (27.2 g, 71.1 mmol) is dissolved in DCM solution (200 mL), and tert-butyldimethylsilyl chloride (TBSCL) (23.6 g, 156.4 mmol, 2.2 eq.) and imidazole (12.1 g, 177.8 mmol, 2.5 eq.) are added to obtain a mixture. After reacting of the mixture at the room temperature for 4 h, the mixture is quenched by adding water (200 mL), washed, separated, and concentrated to obtain a crude product. A flash column chromatography with a silica gel pad is performed on the crude product to obtain the compound 22 (43.4 g, a total yield of 100%).

The compound 22 is detected through $^1$H NMR, $^{13}$C NMR and HRMS, the compound 22 is a pure compound, and performance indicators or characterization data of the compound 22 are as follows: $^1$H NMR (400 MHZ, CHCl$_3$): δ 7.50 (s, 1H), 7.13 (dt, J=7.5, 1.1 Hz, 2H), 7.00-6.94 (m, 2H), 6.24 (s, 1H), 4.98 (dt, J=19.8, 7.0 Hz, 2H), 4.53 (dd, J=12.4, 7.1 Hz, 1H), 4.28 (dd, J=12.4, 7.1 Hz, 1H), 3.63 (s, 3H), 3.49 (ddt, J=12.5, 7.0, 1.1 Hz, 1H), 3.23 (ddt, J=12.4, 7.2, 1.1 Hz, 1H), 1.44 (s, 9H), 1.03 (s, 9H), 0.98 (s, 9H), 0.21 (s, 6H), 0.08 (s, 6H); $^{13}$C NMR (101 MHz, CHCl$_3$): δ 171.89, 170.44, 155.69, 154.23, 130.44, 129.76, 119.74, 79.69, 65.53, 56.85, 54.42, 53.19, 37.95, 28.34, 25.87, 25.43, 18.27, 18.22, -4.39, -5.44; HRMS (m/z): calculated for C$_{30}$H$_{54}$N$_2$NaO$_7$Si$_2$$^+$ ([M+Na]$^+$): 633.3362, found 633.3351.

(7) A synthesis process of a compound 24 is as follows:

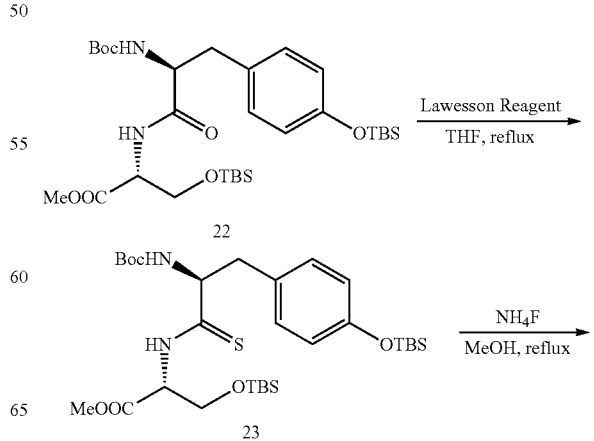

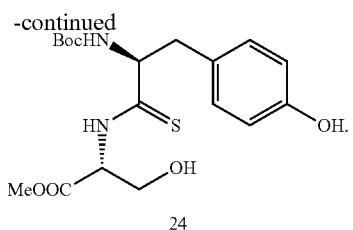

24

The compound 22 (43.4 g, 71.1 mmol) is dissolved in an anhydrous THF (200 mL) solution, and a Lawesson's reagent (34.5 g, 85.3 mmol, 1.2 eq.) is added to obtain a mixture. After reacting of the mixture at a temperature of 70° C. for 14 h, and restoring to the room temperature, the mixture is quenched by adding water (150 mL), concentrated to remove THF therein, and extracted and concentrated with EA to obtain a crude product compound 23.

A MeOH solution (100 mL) of the crude product compound 23 is prepared, and $NH_4F$ (13.2 g, 55.5 mmol, 5.0 eq.) is added to obtain a mixture. After reacting of the mixture at a temperature of 80° C. for 2 h, stop heating and restoring to the room temperature, the mixture is quenched by adding water (100 mL), concentrated to remove MeOH therein, extracted with EA, and concentrated to obtain a crude product. The crude product is purified through a column chromatography (PE/EA=2:1 to 1:1, volume/volume abbreviated as V/V) to obtain the compound 24 (19.8 g, a total yield of 70%).

The compound 24 is detected through $^1H$ NMR, $^{13}C$ NMR and HRMS, the compound 24 is a pure compound, and performance indicators or characterization data of the compound 24 are as follows: $^1H$ NMR (400 MHZ, $CHCl_3$): δ 7.34 (s, 1H), 7.13 (dt, J=7.4, 1.1 Hz, 2H), 6.81-6.70 (m, 2H), 5.83 (t, J=7.0 Hz, 1H), 5.74 (s, 1H), 5.18 (t, J=7.1 Hz, 1H), 4.64 (s, 1H), 4.40 (ddd, J=12.6, 7.1, 5.6 Hz, 1H), 4.20 (ddd, J=12.5, 7.1, 5.5 Hz, 1H), 3.63 (s, 3H), 3.06 (ddt, J=12.5, 7.0, 1.0 Hz, 1H), 2.72 (ddt, J=12.5, 7.2, 1.1 Hz, 1H), 1.52 (t, J=5.5 Hz, 1H), 1.44 (s, 9H); $^{13}C$ NMR (101 MHz, $CHCl_3$): δ 200.49, 170.97, 156.87, 156.33, 130.63, 130.02, 115.82, 79.69, 63.08, 62.84, 55.30, 53.19, 37.71, 28.34; HRMS (m/z): calculated for $C_{18}H_{26}N_2NaO_6S^+$ ([M+Na]$^+$): 421.1404, found 421.1386.

(8) A synthesis process of a compound 25 is as follows:

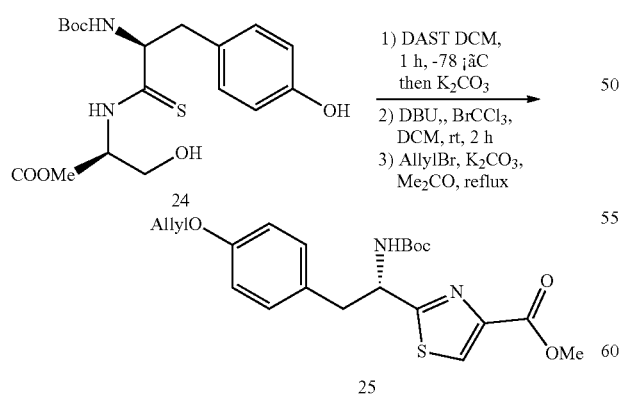

Under a nitrogen protection, the compound 24 (19.8 g, 49.7 mmol) is dissolved in anhydrous THF (80 mL), after cooling to a temperature of −50° C., diethylaminosulfur trifluoride (DAST) (16.5 mL, 125 mmol, 2.5 eq.) is slowly added dropwise, and then stirring is performed for 2 h to thereby obtain a system. $NaHCO_3$ (12.5 g, 149.1 mmol, 3.0 eq.) is added into the system, after restoring naturally to the room temperature and stirring for 1 h, the system is quenched by adding saturated $NaHCO_3$ solution, concentrated to remove THF therein, washed and extracted by adding DCM, dried with anhydrous $Na_2SO_4$ solid, filtered, concentrated under reduced pressure to obtain a first intermediate.

The first intermediate obtained in the previous step is dissolved in anhydrous DCM solution (200 mL), and 1,8-diazabicyclo[5.4.0]undec-7-ene (DBU) (14.8 mL, 99.4 mmol, 2.0 eq.) and bromotrichloro methane ($CBrCl_3$) (9.9 mL, 99.4 mmol, 2.0 eq.) are added to obtain a mixture. After reacting of the mixture at the room temperature for 2 h, the mixture is concentrated to obtain a crude product. The crude product is dissolved in EA solution (100 mL) to obtain a crude product solution. the crude product solution is washed for three times by hydrochloric acid with a concentration of 2N to thereby obtain an organic phase. The organic phase is dried with anhydrous $Na_2SO_4$, filtered, and concentrated to obtain a second intermediate (16.2 g).

The second intermediate (16.2 g, 42.8 mmol) obtained in the previous step is dissolved in acetone solution (100 mL), and potassium carbonate ($K_2CO_3$) (17.7 g, 128.4 mmol, 3.0 eq.) and allyl bromide (9.4 mL, 85.6 mmol, 2.0 eq.) are added to obtain a mixture. After reacting of the mixture at a temperature of 60° C. for 12 h, and restoring to the room temperature, the mixed solution is directly filtered and concentrated to obtain the compound 25 (15.8 g, a total yield of 88%).

The compound 25 is detected through $^1H$ NMR, $^{13}C$ NMR and HRMS, the compound 25 is a pure compound, and performance indicators or characterization data of the compound 25 are as follows: $^1H$ NMR (400 MHZ, $CHCl_3$): δ 8.10 (s, 1H), 7.21 (dt, J=7.6, 1.1 Hz, 2H), 6.93-6.80 (m, 2H), 6.06 (dtd, J=16.8, 9.7, 2.7 Hz, 1H), 5.88 (t, J=7.0 Hz, 1H), 5.59 (ddd, J=13.8, 10.0, 1.8 Hz, 1H), 5.34 (ddd, J=16.7, 13.9, 1.8 Hz, 1H), 5.19 (s, 1H), 4.90-4.75 (m, 2H), 3.96 (s, 3H), 3.41 (ddt, J=12.6, 7.0, 1.1 Hz, 1H), 3.18 (ddt, J=12.5, 7.0, 1.0 Hz, 1H), 1.44 (s, 9H); $^{13}C$ NMR (101 MHz, $CHCl_3$); δ 169.83, 162.00, 157.94, 156.87, 146.40, 132.73, 131.05, 130.57, 127.12, 117.83, 115.06, 79.69, 67.72, 53.94, 52.30, 40.65, 28.34; HRMS (m/z): calculated for $C_{21}H_{26}N_2NaO_5S^+$ ([M+Na]$^+$): 441.1455, found 441.1445.

(9) A synthesis process of a compound 26 is as follows:

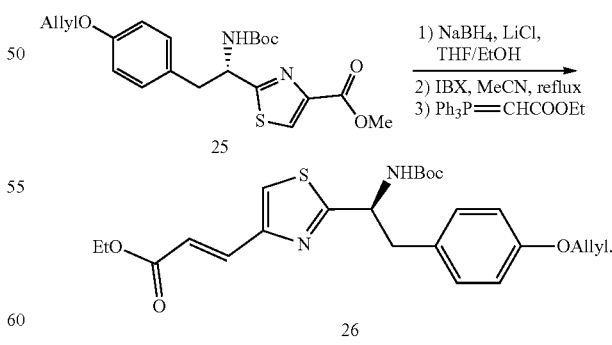

The compound 25 (15.8 g, 37.8 mmol) is dissolved in anhydrous THF solution (80 mL), and the LiCl (6.4 g, 151.2 mmol, 4.0 eq.) and $NaBH_4$ solid (5.7 g, 151.2 mmol, 4.0 eq.) are added to obtain a system. EtOH solution (90 mL) is added into the system to obtain a mixture. After reacting of the mixture at a temperature of 60° C. for 18 h, and restoring to the room temperature, the mixture is quenched by adding water (90 mL), stirred until the mixture clarifies, concentrated to remove the THF and the EtOH, extracted by adding EA, dried with the anhydrous Na$_2$SO$_4$ solid, filtered, concentrated to obtain a first intermediate.

The first intermediate obtained in the previous step is dissolved in methyl sulfoxide (DMSO) (40 mL), and the IBX (10.2 g, 36.6 mmol, 1.2 eq.) is added to obtain a mixture. After reacting of the mixture at the room temperature for 1 h, the mixture is washed by adding the water (100 mL), extracted by adding EA (80 mL) and filtered to obtain a filtrate. The filtrate is stratified by standing to obtain an aqueous phase. The aqueous phase is extracted for three times with EA to obtain organic phases. The organic phases are merged, washed by saturated salt water, dried with anhydrous Na$_2$SO$_4$, filtered, and concentrated under reduced pressure to obtain a second intermediate.

The second intermediate obtained in the previous step is dissolved in anhydrous DCM (150 mL) to obtain a mixture. A Wittig reagent (9.2 g, 27.7 mmol, 1.1 eq.) is added to obtain the mixture. After reacting of the mixture at the room temperature for 1 h, silica gel is added into the mixture to perform a column chromatography with a dry sampling method (PE/EA=4:1, V/V) on the reaction solution to obtain the compound 26 (10.7 g, a total yield of 93%).

The compound 26 is detected through $^1$H NMR, $^{13}$C NMR and HRMS, the compound 26 is a pure compound, and performance indicators or characterization data of the compound 26 are as follows: $^1$H NMR (400 MHZ, CHCl$_3$): δ 7.93 (s, 1H), 7.71 (d, J=15.0 Hz, 1H), 7.28 (dt, J=7.6, 1.1 Hz, 2H), 6.90-6.82 (m, 2H), 6.28 (d, J=15.2 Hz, 1H), 6.06 (dtd, J=16.8, 9.9, 2.3 Hz, 1H), 5.66 (t, J=7.0 Hz, 1H), 5.59 (ddd, J=13.9, 10.1, 1.9 Hz, 1H), 5.41 (s, 1H), 5.35 (dd, J=16.8, 1.9 Hz, 1H), 4.89-4.82 (m, 1H), 4.77 (dd, J=12.3, 9.7 Hz, 1H), 4.33 (dq, J=11.9, 6.0 Hz, 1H), 4.24 (dq, J=12.2, 6.0 Hz, 1H), 3.28 (ddt, J=12.3, 7.0, 1.0 Hz, 1H), 3.00 (ddt, J=12.3, 7.0, 1.0 Hz, 1H), 1.44 (s, 9H), 1.31 (t, J=6.0 Hz, 3H); $^{13}$C NMR (101MHz, CDCl3): δ 170.13, 166.95, 157.94, 156.87, 150.72, 133.80, 132.73, 131.05, 130.57, 123.07, 117.83, 117.27, 115.06, 79.69, 67.72, 60.58, 53.94, 40.65, 28.34, 14.31; HRMS (m/z): calculated for C$_{24}$H$_{30}$N$_2$NaO$_5$S$^+$ ([M+Na]$^+$): 481.1768, found 481.1748.

(10) A synthesis process of a compound 27 is as follows:

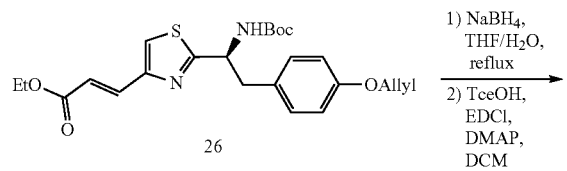

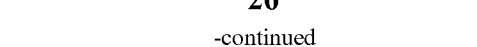

The compound 26 (10.7 g, 23.3 mmol) is dissolved in THF (50 mL), an a sodium hydroxide (NaOH) (1.9 g, 46.6 mmol, 2.0 eq.) aqueous solution (50 mL) and the EtOH (50 mL) are added to obtain a mixture. After reacting of the mixture at the room temperature for 4 h, the mixture is concentrated to remove the solvent and acidified by hydrochloric acid with a concentration of 2 N to adjust pH thereof to 4, to thereby precipitate a solid. The solid is filtered, washed by distilled water, and dried in an oven at a temperature of 80° C. for 12 h to obtain a white solid.

The above white solid is dissolved in anhydrous DCM (100 mL), and trichloroethanol (3.3 mL, 35 mmol, 1.5 eq.), EDCI (8.9 g, 46.6 mmol, 2.0 eq.) and DMAP (2.8 g, 23.3 mmol, 1.0 eq.) are added therein to obtain a mixture. After reacting of the mixture at the room temperature for 12 h, the mixture is concentrated to remove the DCM to obtain an intermediate. The intermediate is dissolved in EA to obtain an intermediate solution. The intermediate solution is washed by hydrochloric acid with a concentration of 2 N to thereby obtain an organic phase. The organic phase is washed by saturated salt water, dried with anhydrous Na$_2$SO$_4$, filtered, and precipitated to obtain the compound 27 (12.6 g, a total yield of 96%).

The compound 27 is detected through $^1$H NMR, $^{13}$C NMR and HRMS, the compound 27 is a pure compound, and performance indicators or characterization data of the compound 27 are as follows: $^1$H NMR (400 MHZ, CHCl$_3$): δ 7.93 (s, 1H), 7.81 (d, J=15.0 Hz, 1H), 7.09 (dt, J=7.6, 1.1 Hz, 2H), 6.82-6.74 (m, 2H), 6.42 (d, J=15.0 Hz, 1H), 6.06 (dtd, J=16.8, 9.9, 2.1 Hz, 1H), 5.87 (t, J=7.1 Hz, 1H), 5.59 (ddd, J=13.7, 10.1, 1.9 Hz, 1H), 5.38-5.27 (m, 3H), 5.19 (s, 1H), 4.91 (dq, J=12.5, 2.0 Hz, 1H), 4.73 (dd, J=12.4, 10.0 Hz, 1H), 3.31-3.21 (m, 1H), 3.08 (ddt, J=12.5, 7.0, 1.1 Hz, 1H), 1.44 (s, 9H); $^{13}$C NMR (101 MHz, CHCl$_3$): δ 170.13, 168.82, 157.94, 156.87, 150.72, 133.80, 132.73, 131.05, 130.57, 123.07, 117.83, 117.27, 115.06, 95.14, 79.69, 73.88, 67.72, 53.94, 40.65, 28.34; HRMS (m/z): calculated for C$_{24}$H$_{27}$C$_{13}$N$_2$NaO$_5$S$^+$ ([M+Na]$^+$): 583.0598, found 583.0588.

(11) A synthesis process of a compound 28 is as follows:

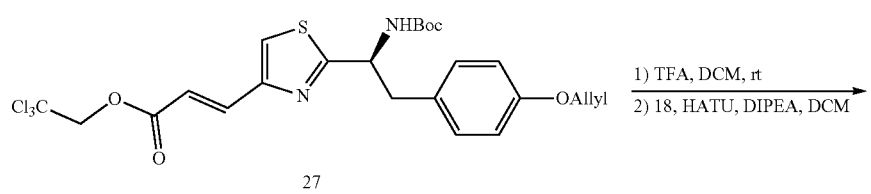

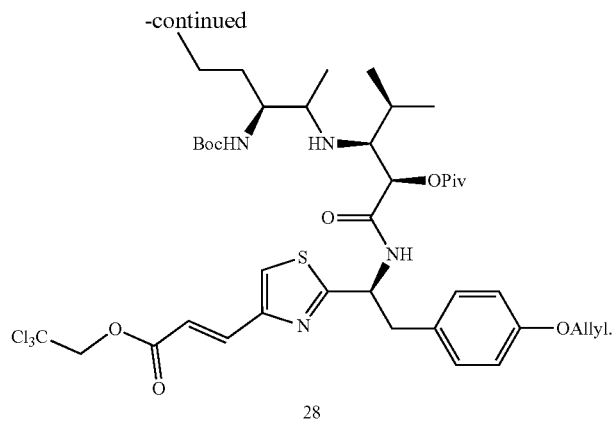

The compound 27 (15.0 g, 26.7 mmol) is dissolved in DCM solution (200 mL), and TFA (30 mL) is added to obtain a mixture. After stirring of the mixture for reacting at the room temperature for 3 h, saturated sodium bicarbonate solution is slowly added dropwise to neutralize the mixture to make pH=8 to obtain a neutralized solution. The neutralize solution is extracted for three times with DCM solution (300 mL) to obtain organic phases. The organic phases are merged, dried with anhydrous $Na_2SO_4$, and concentrated under reduced pressure to obtain an intermediate amine.

The intermediate amine is dissolved in anhydrous DCM (500 mL), HATU (15.2 g, 40 mmol) and the compound 18 (11.6 g, 26 mmol) are sequentially added, and after cooling to the temperature of 0° C., DIPEA (8.3 mL, 50 mmol) is slowly added dropwise to react for 30 min to obtain a mixture. After heating of the mixture to the room temperature for reacting for 14 h, an organic phase is obtained. The organic phase is sequentially washed by diluted hydrochloric acid (300 mL) with a concentration of 2 M, washed by saturated sodium bicarbonate solution (300 mL), dried with anhydrous $Na_2SO_4$, and concentrated under reduced pressure to obtain a crude product. PE and EA with a ratio of 2:1 are used as an eluent to perform a flash column chromatography on the crude product to obtain the compound 28 (18.5 g, a total yield of 80%).

The compound 28 is detected through $^1$H NMR, $^{13}$C NMR and HRMS, the compound 28 is a pure compound, and performance indicators or characterization data of the compound 28 are as follows: $^1$H NMR (400MHZ, $CHCl_3$): δ 7.64 (d, J=15.5 Hz, 1H), 7.39 (s, 1H), 7.10 (d, J=7.3 Hz, 1H), 6.83 (d, J=8.6 Hz, 2H), 6.74 (t, J=11.7 Hz, 3H), 6.51 (d, J=10.0 Hz, 1H), 6.00 (ddd, J=22.4, 10.5, 5.3 Hz, 1H), 5.47 (dd, J=8.6, 6.1 Hz, 2H), 5.36 (dd, J=17.3, 1.4 Hz, 1H), 5.24 (dd, J=10.5, 1.2 Hz, 1H), 4.90 (d, J=10.0 Hz, 1H), 4.83 (t, J=9.5 Hz, 2H), 4.48-4.44 (m, 2H), 4.35 (t, J=8.3 Hz, 1H), 3.82 (dd, J=14.3, 8.0 Hz, 1H), 3.24 (dd, J=13.7, 4.5 Hz, 1H), 3.10 (dd, J=13.8, 7.5 Hz, 1H), 1.52-1.42 (m, 3H), 1.39 (s, 9H), 1.25 (d, J=11.9 Hz, 9H), 1.11 (dd, J=6.3, 3.5 Hz, 4H), 0.91 (d, J=6.6 Hz, 3H), 0.82 (t, J=7.2 Hz, 3H), 0.71 (t, J=7.1 Hz, 3H); $^{13}$C NMR (100 MHz, $CHCl_3$): δ 176.26, 171.60, 170.19, 167.93, 165.15, 157.59, 155.97, 150.51, 137.82, 133.14, 130.60, 127.40, 122.80, 118.97, 117.53, 114.63, 94.99, 80.00, 74.11, 72.65, 68.65, 54.13, 52.54, 40.74, 38.95, 36.36, 33.35, 28.18, 27.01, 25.06, 18.70, 15.58, 13.59, 10.89; HR-ESIMS m/z: calculated for $C_{41}H_{57}Cl_3N_4O_9SNa^+$ [M+Na]$^+$: 909.2912, found 909.2915.

(12) A synthesis process of a compound 29 is as follows:

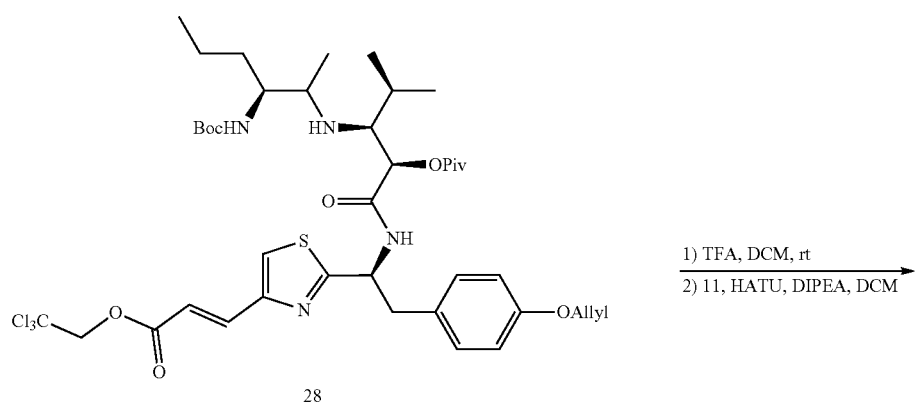

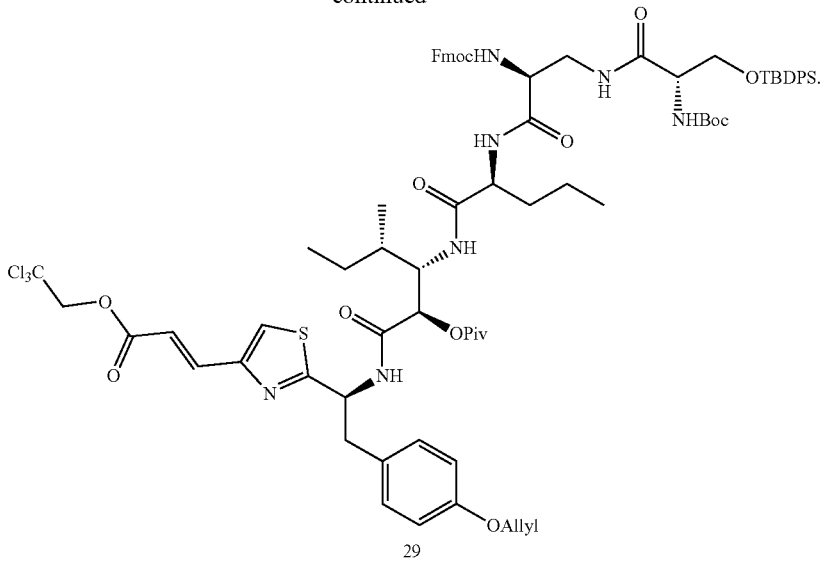

The compound 28 (17.8 g, 20 mmol) is dissolved in DCM solution (200 mL), and TFA (30 mL) is added to obtain a mixture. After stirring of the mixture for reacting at the room temperature for 3 h, saturated sodium bicarbonate solution is slowly added dropwise to neutralize the mixture to make pH=8 to obtain a neutralized solution. The neutralize solution is extracted for three times with DCM solution (300 mL) to obtain organic phases. The organic phases are merged, dried with the anhydrous $Na_2SO_4$, and concentrated under reduced pressure to obtain an intermediate amine.

The above intermediate amine is dissolved in anhydrous DCM (500 mL), HATU (11.4 g, 30 mmol) and the compound 11 (15.0 g, 20 mmol) are sequentially added, and after cooling to the temperature of 0° C., DIPEA (6.6 mL, 40 mmol) is slowly added dropwise to react for 30 min to obtain a mixture. After heating of the mixture to the room temperature to react for 14 h, an organic phase is obtained. The organic phase is sequentially washed by diluted hydrochloric acid (300 mL) with a concentration of 2 M, washed by saturated sodium bicarbonate solution (300 mL), dried with anhydrous $Na_2SO_4$, and concentrated under reduced pressure to obtain a crude product. PE and EA with a ratio of 1:1 are used as an eluent to perform a flash column chromatography on the crude product to obtain the compound 29 (21.3 g, a total yield of 70%).

The compound 29 is detected through $^1H$ NMR, $^{13}C$ NMR and HRMS, the compound 29 is a pure compound, and performance indicators or characterization data of the compound 29 are as follows: $^1H$ NMR (500 MHZ, $CHCl_3$): δ 7.93-7.85 (m, 3H), 7.78-7.63 (m, 6H), 7.61-7.43 (m, 6H), 7.46-7.36 (m, 6H), 7.14-7.06 (m, 3H), 6.80-6.70 (m, 4H), 6.30 (d, J=15.0 Hz, 1H), 6.24 (s, 2H), 6.16-6.00 (m, 2H), 5.67-5.54 (m, 3H), 5.34 (ddd, J=16.7, 13.8, 1.9 Hz, 1H), 5.16 (t, J=7.0 Hz, 1H), 4.83 (dd, J=12.4, 9.9 Hz, 1H), 4.77-4.67 (m, 4H), 4.42 (dd, J=12.5, 7.0 Hz, 1H), 4.37-4.22 (m, 3H), 4.17 (dd, J=12.4, 7.1 Hz, 1H), 3.81 (d, J=12.3 Hz, 1H), 3.43 (dd, J=12.5, 7.0 Hz, 1H), 3.29 (ddt, J=12.5, 7.0, 1.1 Hz, 1H), 3.10 (ddt, J=12.5, 6.9, 1.1 Hz, 1H), 2.69 (tdd, J=12.9, 3.5, 2.2 Hz, 1H), 2.08-1.96 (m, 1H), 1.94-1.82 (m, 1H), 1.44 (s, 9H), 1.08 (d, J=20.0 Hz, 18H), 0.96-0.87 (m, 6H), 0.81 (t, J=8.0 Hz, 3H), 0.37 (dqd, J=12.2, 7.9, 1.7 Hz, 1H); $^{13}C$ NMR (125 MHz, $CHCl_3$): δ 177.23, 172.54, 172.02, 170.28, 170.13, 169.33, 168.82, 158.44, 157.94, 156.03, 150.72, 143.56, 141.18, 134.46, 133.80, 133.76, 132.73, 131.05, 130.57, 129.97, 128.81, 127.07, 126.38, 125.48, 123.07, 121.08, 117.83, 117.27, 115.06, 95.14, 79.69, 74.61, 73.88, 67.72, 66.72, 64.70, 54.73, 54.68, 54.31, 54.03, 52.98, 47.37, 40.72, 38.98, 34.38, 34.30, 28.34, 27.10, 26.83, 26.35, 15.29, 13.18, 11.50; HR-ESIMS m/z: calculated for $C_{78}H_{96}C_{13}N_7O_{14}SSiNa^+$ $[M+Na]^+$: 1542.5571, found 1542.5575.

(13) A synthesis process of a key intermediate compound 2 is as follows:

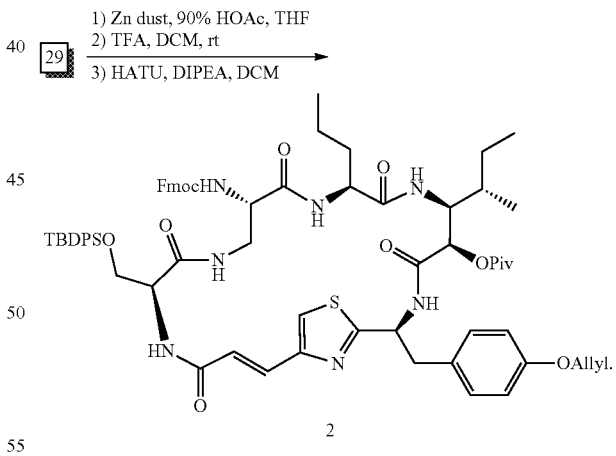

The compound 29 (10.0 g, 6.6 mmol) is dissolved in THF (200 mL), and acetic acid (50 mL) with a concentration of 90% and zinc dust (8.6 g, 132 mmol) are added to obtain a mixture. After stirring of the mixture for reacting at the room temperature for 2 h, the mixture is concentrated under reduced pressure to remove the THF, and diluted by adding water (500 mL) to obtain a diluted solution. A saturated sodium bicarbonate solution is slowly added dropwise to neutralize the diluted solution to pH=8 to obtain a neutralized solution. The neutralize solution is extracted for three times with DCM solution (500 mL) to obtain an extracted solution. The extracted solution is filtered to remove the zinc dust to obtain a filtrate. The filtrate is separated into an organic phase and an aqueous phase. The aqueous phase is extracted for twice with the DCM solution (400 mL) to obtain organic phases. The organic phases are merged, dried with the anhydrous $Na_2SO_4$, and concentrated under reduced pressure to obtain an intermediate acid.

The above intermediate acid is dissolved in DCM solution (200 mL), and TFA (30 mL) is added to obtain a mixture. After stirring of the mixture for reacting at the room temperature for 3 h, the mixture is concentrated under reduced pressure to obtain an intermediate amine.

The above intermediate amine is dissolved in DCM solution (3000 mL), and HATU (7.5 g, 19.8 mmol) and DIPEA (5.0 mL, 30 mmol) are added to obtain a mixture. After stirring of the mixture to react at the room temperature for 1 day, the mixture is concentrated under reduced pressure to obtain a crude product. PE and EA with a ratio of 1:1 are used as an eluent to perform a flash column chromatography on the crude product to obtain the compound 2 (6.7 g, a total yield of 80%).

The compound 2 is detected through $^1$H NMR, $^{13}$C NMR and HRMS, the compound 2 is a pure compound, and performance indicators or characterization data of the compound 2 are as follows: $^1$H NMR (500 MHz, $CHCl_3$): δ 9.45 (s, 1H), 9.32 (s, 1H), 8.30 (s, 1H), 7.82-7.74 (m, 3H), 7.67 (ddq, J=6.8, 4.5, 2.7, 2.3 Hz, 4H), 7.61 (s, 1H), 7.56-7.48 (m, 3H), 7.48-7.39 (m, 2H), 7.42-7.36 (m, 6H), 7.09 (dt, J=7.6, 1.1 Hz, 2H), 6.82-6.76 (m, 2H), 6.67 (s, 1H), 6.60 (d, J=15.0 Hz, 1H), 6.46 (d, J=15.0 Hz, 1H), 6.24 (s, 1H), 6.16-6.00 (m, 2H), 5.69 (t, J=7.0 Hz, 1H), 5.59 (ddd, J=13.8, 10.0, 1.7 Hz, 1H), 5.41 (s, 1H), 5.34 (ddd, J=16.9, 13.8, 1.8 Hz, 1H), 5.16 (t, J=7.0 Hz, 1H), 4.81-4.68 (m, 5H), 4.53 (t, J=7.0 Hz, 1H), 4.46-4.32 (m, 2H), 4.17 (dd, J=12.5, 7.0 Hz, 1H), 4.08 (dd, J=12.6, 7.1 Hz, 1H), 3.62 (dd, J=12.5, 7.0 Hz, 1H), 3.35 (ddt, J=12.4, 7.1, 1.0 Hz, 1H), 3.09 (ddt, J=12.5, 7.0, 1.1 Hz, 1H), 2.07-1.89 (m, 2H), 1.81 (tt, J=12.6, 2.1 Hz, 1H), 1.30-1.15 (m, 2H), 1.08 (d, J=20.0 Hz, 19H), 0.92 (dd, J=9.1, 7.3 Hz, 6H), 0.85 (t, J=8.0 Hz, 3H); $^{13}$C NMR (125 MHz, $CHCl_3$): δ 177.23, 172.54, 172.02, 170.28, 170.13, 166.76, 158.44, 157.94, 150.10, 143.56, 141.18, 134.46, 133.76, 133.39, 132.73, 131.05, 130.57, 129.97, 128.81, 127.07, 126.38, 125.48, 123.07, 121.08, 119.85, 117.83, 115.06, 74.61, 67.72, 66.72, 64.70, 54.68, 54.40, 54.31, 54.03, 52.98, 47.37, 40.72, 38.98, 34.38, 34.30, 27.10, 26.83, 26.35, 15.29, 13.18, 11.50; HR-ESIMS m/z: calculated for $C_{71}H_{85}N_7O_{11}SSiNa^+$ $[M+Na]^+$: 1294.5797, found 1294.5801.

(14) A synthesis process of a compound 1a is as follows:

1) DEA, MeCN, rt
2) $HCO_2Et$, Seal tube, 80° C.
3) $NH_4F$, MeOH, reflux
4) MsCl, $Et_3N$, DCM, rt, 2 h
5) KSAc, DMF, rt, 2 h

[2] ⟶

6) Oxone (20 eq.), AcOH, AcOK, 65° C.
7) $Et_3N/H_2O$/MeOH, reflux, 2 d
8) IBX, DMSO, 50° C., 2 h
9) $SeO_2$, HOAc, dioxane, reflux
10) 1.0M NaCl, MeOH/$H_2O$, rt

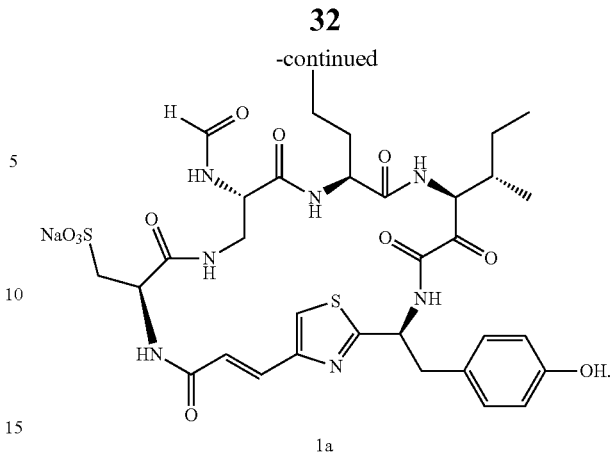

1a

The compound 2 (6.0 g, 4.7 mmol) is dissolved in acetonitrile (200 mL), and diethylamine (DEA) (20 mL) is then added to thereby obtain a mixture. After stirring of the mixture for reacting at the room temperature for 2 h, the mixture is concentrated under reduced pressure to obtain a intermediate amine.

The intermediate amine is dissolved in ethyl formate (50 mL), sealed (i.e., seal tube) at 80° C. for 10 hours for reacting, and cooled to the room temperature and concentrated under reduced pressure to obtain a first intermediate.

The first intermediate is dissolved in methanol (200 mL), and ammonium fluoride ($NH_4F$) solid (9.8 g, 265 mmol) is added to thereby obtain a mixture. After heating and refluxing of the mixture for reacting for 12 h, the mixture is concentrated under reduced pressure to remove the methanol to obtain a residue. The residue is dissolved in EA (800 mL), washed with saturated sodium bicarbonate solution (200 mL), dried with anhydrous sodium sulfate, and concentrated under reduced pressure to obtain a second intermediate.

The second intermediate is dissolved in anhydrous dichloromethane (200 mL), and triethylamine (1.5 mL, 10.6 mmol) is added to obtain a mixture. After cooling of the mixture to a temperature of 0° C., methanesulfonyl chloride (0.6 mL, 8 mmol) is slowly added dropwise to the mixture to react for 30 min, and then the mixture is heated to the room temperature for 2 h to obtain a reaction solution. The reaction solution is diluted with DCM (500 mL), and sequentially washed with 1M of dilute hydrochloric acid (200 mL), washing with saturated sodium bicarbonate solution (200 mL), dried with anhydrous sodium sulfate, and concentrated under reduced pressure to obtain a third intermediate.

The third intermediate is dissolved in DMF (20 mL), and then potassium thioacetate (KSAc) (6.0 g, 53 mmol) is added to obtain a mixture. After stirring of the mixture at the room temperature for 4 h, the mixture is quenched by adding water (500 mL), and extracted with EA (400 mL) twice to obtain organic phases. The organic phases are merged, washed with saturated sodium chloride aqueous solution (300 mL), dried with anhydrous sodium sulfate, and concentrated under reduced pressure to obtain a fourth intermediate.

The fourth intermediate is dissolve in acetic acid (200 mL), and potassium acetate (KAc) (65 g, 662 mmol) and potassium monopersulphate triple salt (Oxone) (65.2 g, 106 mmol) are added to obtain a solution. The solution is heated to 65° C. for reacting for 14 h, then cooled to 0° C., and is quenched by adding water (600 mL) to obtain a reaction solution. Then sodium hydroxide solid is slowly added to the reaction solution to neutralize the reaction solution to pH=8 to obtain a neutralized solution. The neutralized solution is extracted with EA (400 mL) for three times to obtain organic phases. The organic phases are merged, wash withed saturated sodium chloride aqueous solution (300 mL), dried with anhydrous sodium sulfate, and concentrated under reduced pressure to obtain intermediate sulfonic acid.

The intermediate sulfonic acid is dissolved in methanol (300 mL), and triethylamine (30 mL) and water (30 mL) are added to obtain a mixture. After heating and refluxing of the mixture for reacting for 2 days, the mixture is concentrated under reduced pressure to remove all solvents, and fully dried to obtain an fifth intermediate.

The fifth intermediate is dissolved in DMSO (40 mL), and IBX (4.5 g, 15.9 mmol) is added to obtain a mixture. After heating of the mixture to 60° C. for reacting for 2 h, the mixture is quenched by adding water (500 mL), and extracted with ethyl acetate (300 mL) for three times to obtain an organic phase. The organic phase is washed with saturated sodium chloride aqueous solution (200 mL), dried with anhydrous sodium sulfate, and concentrate under reduced pressure to obtain a sixth intermediate.

The sixth intermediate is dissolved in 1,4-dioxane (100 mL), and acetic acid (1.5 mL, 26.5 mmol) and selenium dioxide ($SeO_2$) (1.8 g, 15.9 mmol) are added to obtain a mixture. After heating and refluxing of the mixture for 4 h, the mixture is concentrated under reduced pressure, and silica gel column chromatography is directly performed on the mixture to obtain a crude product intermediate.

The crude product intermediate is dissolved in a mixed solvent of methanol and water (1:1, 10 mL), and then sodium chloride solution (1 M, 5.0 mL) is added to obtain a mixture. After stirring of the mixture at the room temperature for reacting for 1 h, the mixture is concentrated under reduced pressure, and then purified by reversed-phase high performance liquid chromatography (HPLC) to obtain a pure compound 1a (TM) (1.2 g), with an overall yield of 30% through the above 10 steps.

The compound 1a is detected through $^1$H NMR, $^{13}$C NMR and HRMS, the compound 1a is a pure compound, and performance indicators or characterization data of the compound 1a are as follows: $^1$H NMR (500 MHz, $d_6$-DMSO): δ 8.20 (s, 2H), 8.10 (s, 1H), 8.00 (s, 2H), 7.83 (s, 1H), 7.50 (s, 1H), 7.33 (d, J=15.0 Hz, 1H), 7.10 (s, 1H), 7.05-6.99 (m, 2H), 6.78-6.72 (m, 2H), 6.46 (d, J=15.0 Hz, 1H), 6.00 (s, 1H), 5.26 (t, J=6.9 Hz, 1H), 5.16 (t, J=6.9 Hz, 1H), 4.94 (t, J=6.9 Hz, 1H), 4.44 (t, J=6.9 Hz, 1H), 4.26 (d, J=6.9 Hz, 1H), 3.83 (dd, J=12.3, 7.1 Hz, 1H), 3.62 (ddd, J=35.7, 12.4, 7.1 Hz, 2H), 3.40 (dd, J=12.4, 7.0 Hz, 1H), 3.23 (ddt, J=12.2, 6.9, 0.9 Hz, 1H), 2.98 (ddt, J=12.2, 6.9, 1.0 Hz, 1H), 2.34 (hept, J=6.8 Hz, 1H), 2.02 (q, J=7.0 Hz, 1H), 1.72-1.61 (m, 1H), 1.60-1.45 (m, 3H), 1.00 (dq, J=8.8, 7.1 Hz, 1H), 0.92 (t, J=3.9 Hz, 4H), 0.92-0.81 (m, 5H); $^{13}$C NMR (125 MHz, $d_6$-DMSO): δ 196.34, 172.57, 170.99, 170.61, 170.13, 166.76, 163.98, 163.46, 156.33, 150.10, 133.39, 130.75, 129.00, 123.07, 119.85, 115.82, 59.65, 54.03, 53.52, 50.89, 50.31, 48.68, 41.23, 40.65, 36.06, 34.30, 23.40, 19.44, 16.00, 13.18, 11.60; HR-ESIMS m/z:calculated for $C_{33}H_{42}N_7NaO_{11}S_2Na^+$ [M+Na]$^+$: 822.2281, found 822.2284.

An Inhabitation Effect of the Compound 1a (TM) to Main Protease (Mpro) of SARS-CoV-2 Virus
 1. Experimental materials include an Mpro detection kit (78042-2) of the BPS Bioscience company and the TM.
 2. A specific experimental method is as follows. In a black 384-well plate, a blank well group, a negative control well group and a sample well group are set, and a reaction system is 25 μL. The blank well group is added with 12.5 μL of buffer, the negative control well group is added with 10 μL of Mpro and 2.5 μL of buffer, the sample well group is added with 10 μL of Mpro and 2.5 μL of TM solution (respectively with concentrations of 0.001 μM, 0.01 μM, 0.1 μM, 1 μM, 10 μM, 100 μM, 300 μM and 500 μM), and the three groups are incubated at the room temperature for 30 min. Each well is added with 12.5 μL of substrate, after mixing evenly, fluorescence value of each well is immediately detected at Ex/Em=360/460 nm, every 20 seconds, and a dynamic process within 4 h is observed. Two different time points T1 and T2 are selected within a linear range of the dynamic process to obtain fluorescence values (RFUT1 and RFUT2) corresponding to the time points, a slope of the fluorescence values is calculated, and the slope can be regarded as an enzyme activity of each well. A formula of the slope is slope=(RFUT2−RFUT1)/(T2−T1). An enzyme activity of the negative control well group is taken as 100% to calculate a relative enzyme activity of each of the blank well group and the sample well group relative to the negative control well group. A half inhibitory concentration ($IC_{50}$) is calculated through an Origin 2021 software.
 3. Experimental result is as follows.

As shown in FIG. 1, the TM can inhabit an enzyme activity of the Mpro, and a value of $IC_{50}$ is 128.69 μM.

An Inhabitation Effect of the TM to Neutrophil Elastase (NE)
 1. Experimental materials include a NE protease detection kit (ab118971) of an Abcam company and TM.
 2. Experimental methods are as follows. In a black 96-well plate, a blank well group, a negative control well group and a sample well group are set, and a reaction system is 100 μL. The blank well group is added with 75 μL of buffer, the negative control well group is added with 50 μL of NE protease and 25 μL of buffer, the sample well group is added with 50 μL of NE protease and 25 μL of TM solution (respectively with concentrations of 0.00001 μM, 0.0001 μM, 0.001 μM, 0.003 μM, 0.01 μM 0.1 μM, 1 μM, and 10 μM), and the three groups are incubated at a temperature of 37° C. for 5 min. Each well is added with 25 μL of substrate, after mixing evenly, fluorescence value of each well is immediately detected at Ex/Em=400/505 nm, and is detected every 20 seconds, and a dynamic process within a range of 0-40 min is observed. Two different time points (T1 and T2) are selected within a linear range of the dynamic process to obtain fluorescence values (RFUT1 and RFUT2) corresponding to the time points, a slope of the fluorescence values is calculated, and the slope can be regarded as an enzyme activity of each well. A formula of the slope is slope=(RFUT2−RFUT1)/(T2−T1). An enzyme activity of the negative control well group is taken as 100% to calculate a relative enzyme activity of each of the blank well group and the sample well group relative to the negative control well group. A half inhibitory concentration ($IC_{50}$) is calculated through the Origin 2021 software.
 3. Experimental result is as follows.

Figure 2:
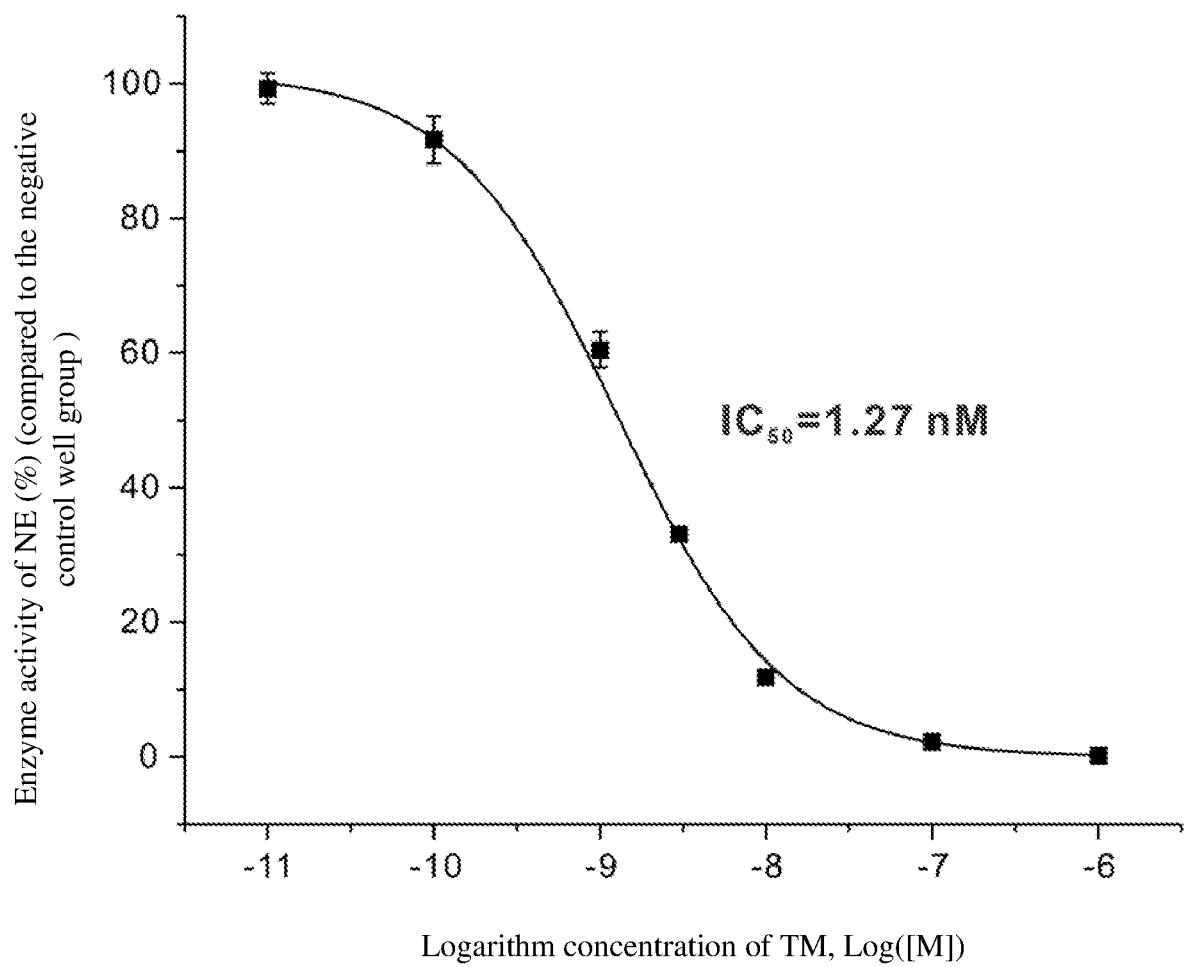
FIG. 2 illustrates a schematic diagram of an enzyme activity of neutrophil elastase (NE) under the inhibiting of the TM according to an embodiment of the disclosure.

As shown in FIG. 2, the TM can inhibit an enzyme activity of the NE, and a value of $IC_{50}$ is 1.27 nanomolar per liter (nM).

From the above experiments, it can be seen the structural analog TM of Cyclotheonellazole A has a strong inhibitory activity on NE, and has the potential to be used in the study of acute lung injury/acute respiratory distress syndrome or disseminated intravascular coagulation of COVID-19.

In the disclosure, based on the total synthetic route of Cyclotheonellazole A, the classical reverse synthesis analysis is utilized, the structural modification is purposefully carried out, a mother nucleus of the natural product remains unchanged, and the structural analog 1a (TM) is obtained by replacing a left side chain with a simple formylamine, thereby confirming the excellent protease inhibitory activity of the structural analog of Cyclotheonellazole A, and having a strong application prospect in the pharmaceutical industry.

The above are merely embodiments of the disclosure and are not intended to limit it, any modifications, equivalent substitutions and improvements made within a spirit and principles of the disclosure shall be included in a scope of protection of the disclosure.

What is claimed is:

1. A synthetic method of a compound 1a, wherein the compound 1a has a structure expressed as follows:

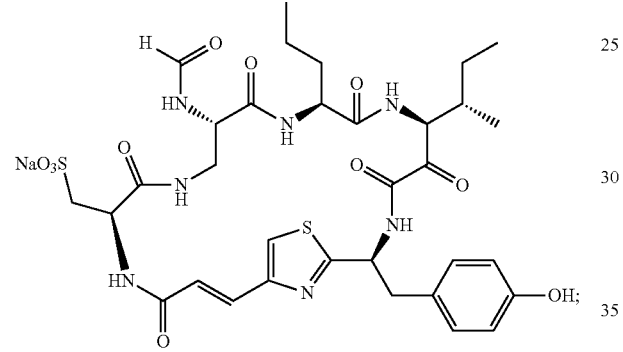

1a and
wherein the synthetic method comprises:
removing a 9-fluorenylmethyloxycarbonyl (Fmoc) protection group from a compound 2 with diethanolamine (DEA) to obtain a first group-removed compound; performing a reaction on the first group-removed compound and ethyl formate ($C_3H_6O_2$) in a condition of seal tube and at a temperature of 80 degrees Celsius (° C.) to obtain formamide ($CH_3NO$); removing a tert-butyldiphenylsilyl (TBDPS) protection group from the formamide with ammonium fluoride ($NH_4F$) to obtain a second group-removed compound; activating a hydroxyl group of the second group-removed compound with methanesulfonyl chloride (MsCl) to obtain activated compound; performing a bimolecular nucleophilic substitution (SN2) reaction on the activated compound with potassium thioacetate (KSAc) to obtain a thioester; oxidizing the thioester with potassium monopersulphate triple salt (Oxone) to obtain a first sulfurous acid; removing a pivaloyl (Piv) group from the first sulfurous acid with triethylamine ($C_6H_{15}N$) in a reflux condition of methanol (MeOH) to obtain a secondary alcohol; oxidizing the secondary alcohol with 2-iodoxybenzoic acid (IBX) to obtain a α-ketoamide; oxidizing the α-ketoamide with selenium dioxide ($SeO_2$) to remove two allyl groups from the α-ketoamide, to thereby obtain a second sulfurous acid; and adding a saturated sodium chloride solution into the second sulfurous acid to obtain the compound 1a;

wherein a specific synthesis process of the compound 1a is as follows:

1) DEA, MeCN, rt
2) HCO$_2$Et, Seal tube, 80° C.
3) NH$_4$F, MeOH, reflux
4) MsCl, Et$_3$N, DCM, rt, 2 h
5) KSAc, DMF, rt, 2 h
6) Oxone (20 eq.), AcOH, AcOK, 65° C.
7) Et$_3$N/H$_2$O/MeOH, reflux, 2 d
8) IBX, DMSO, 50° C., 2 h
9) SeO$_2$, HOAc, dioxane, reflux
10) 1.0M NaCl, MeOH/H$_2$O, rt

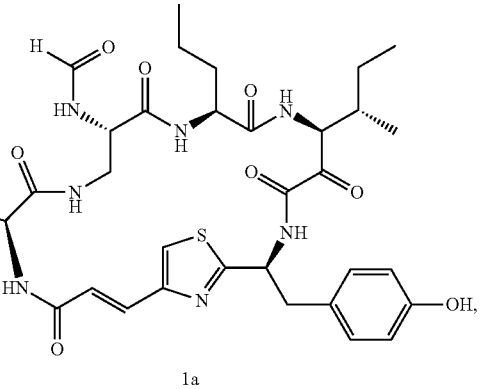

1a wherein a structure of the compound 2 is as follows:

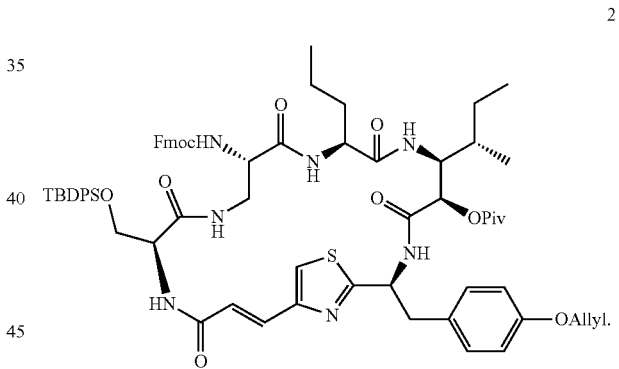

2

2. The synthesis method as claimed in claim 1, wherein a synthesis method of the compound 2 comprises:
performing a condensation reaction on a compound 19 and a compound 20 to obtain a compound 21; protecting a primary alcohol group of the compound 21 with tert-butyldimethylsilyl chloride (TBSCL) to obtain a compound 22; performing a thionation reaction on the compound 22 with a Lawesson's reagent to obtain a compound 23; removing a t-butyldimethylsilyl (TBS) protection group from the compound 23 with NH$_4$F to obtain a compound 24; performing a ring-closing reaction on the compound 24 with diethylaminosulfurtrifluoride (DAST) to obtain a ring-closed compound, oxidizing the ring-closed compound with 1,8-diazabicyclo[5.4.0]undec-7-ene (DBU) and bromotrichloro methane (CBrCl$_3$) to obtain a first oxidized compound, and adding an allyl group into the first oxidized compound to obtain a compound 25; reducing a methyl ester group of the compound 25 with lithium borohydride (BH₄Li) to obtain a reduced compound, oxidizing a primary alcohol group of the reduced compound with IBX to obtain a second oxidized compound, and performing a Wittig reaction on the second oxidized compound to obtain a compound 26; and hydrolyzing an ethyl ester group of the compound 26 with sodium hydroxide (NaOH) to obtain a first hydrolyzed compound, and performing an esterification reaction on the first hydrolyzed compound and trichloroethanol (C₂H₃Cl₃O) to obtain a compound 27;

wherein a specific synthesis process of the compound 27 is as follows:

removing a Boc protection group from the compound 27 with trifluoroacetic acid (TFA) to obtain a third group-removed compound, and performing a peptide grafting reaction on the third group-removed compound and a compound 18 to obtain a compound 28; and removing a Boc protection group from the compound 28 with trifluoroacetic acid to obtain a fourth group-removed compound, and performing a peptide grafting reaction on the fourth group-removed compound and a compound 11 to obtain a compound 29; wherein a specific synthesis process of the compound 29 is as follows:

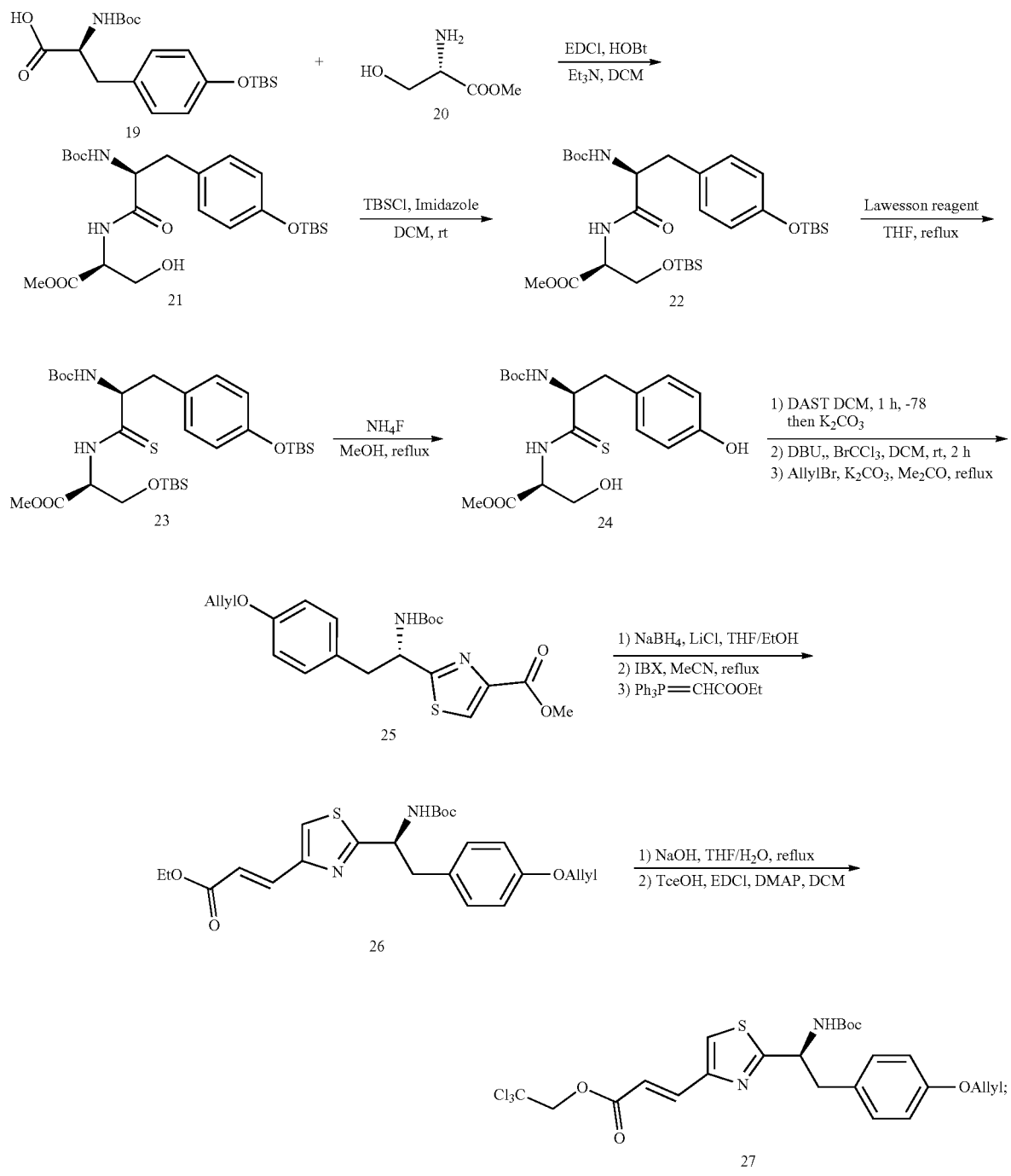

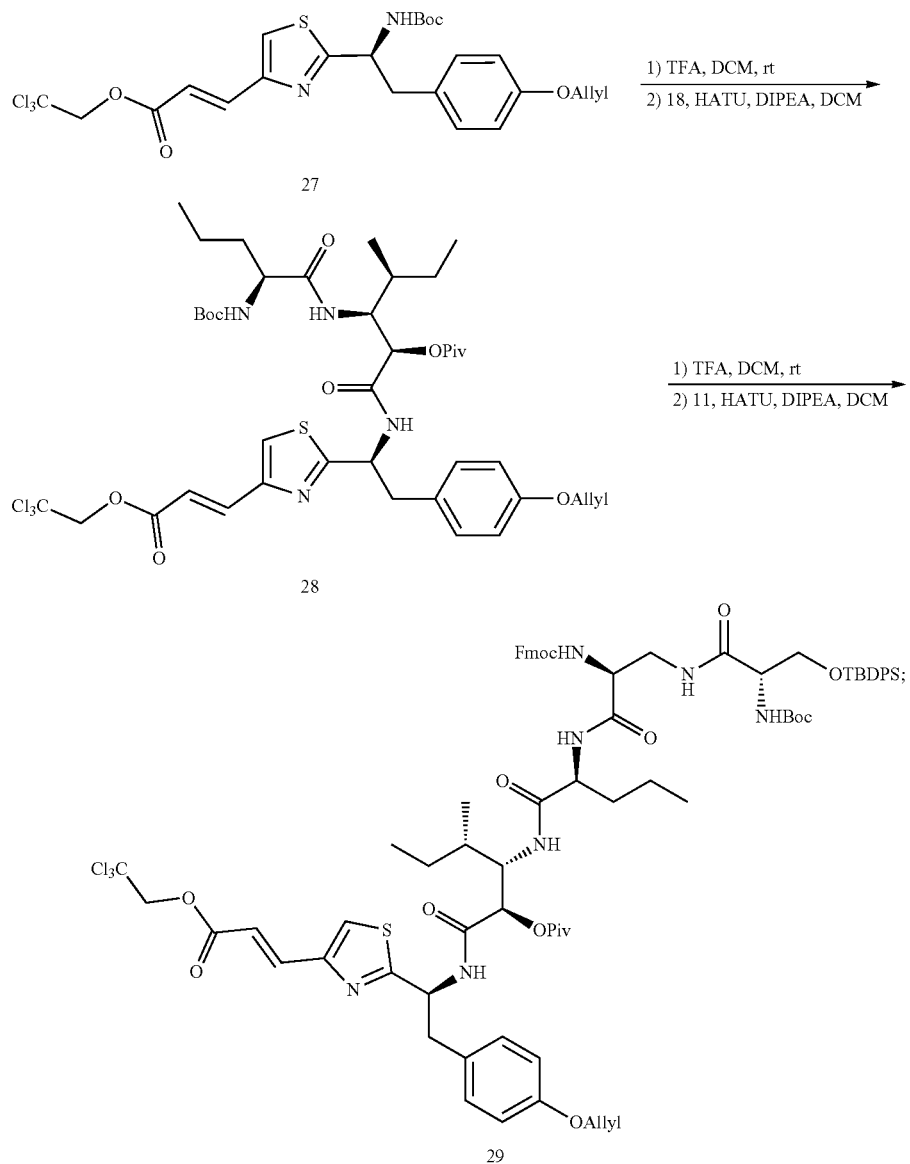

hydrolyzing a trichloroethyl ester group of the compound 29 in an acetic acid solution with a zinc dust to obtain a second hydrolyzed compound, removing a Boc protection group from the second hydrolyzed compound with trifluoroacetic acid to obtain a fifth group-removed compound, and performing an intra-molecular macro-cyclic-closing reaction on the fifth group-removed compound in a dichloromethane (DCM) solution with 2-(7-azabenzotriazol-1-yl)-N,N,N',N'-tetramethyluronium hexafluorophosphate (HATU) to obtain the compound 2; wherein a specific synthesis process of the compound 2 is as follows:

-continued

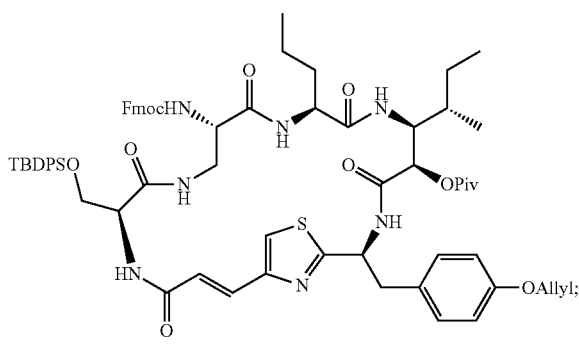

wherein structures of the compound 11 and the compound 18 are as follows:

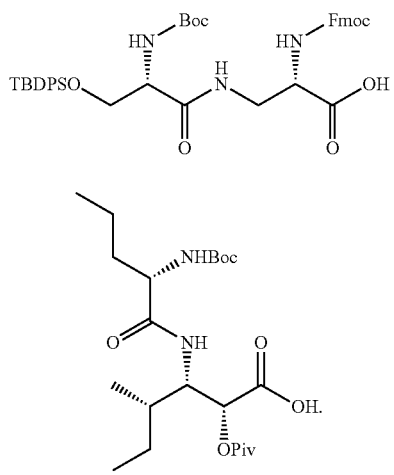

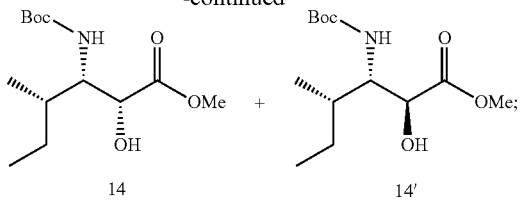

3. The synthesis method as claimed in claim 2, wherein a synthesis method of the compound 18 comprises:

taking a compound 12 as a starting material, performing a methyl esterification on the compound 12 to obtain a methyl esterified compound, protecting an amino group of the methyl esterified compound with di-tert-butyl dicarbonate ($BOC_2O$) to obtain a first intermediate compound, and reducing a methyl ester group of the first intermediate compound with the lithium borohydride to obtain a compound 13; oxidizing a primary alcohol group of the compound 13 with the IBX to obtain an aldehyde, performing a reaction on the aldehyde and acetone cyanohydrin to obtain a second intermediate compound, refluxing and hydrolyzing, by using a MeOH solution of hydrogen chloride, the second intermediate compound without purifying to obtain a third hydrolyzed compound, and protecting an amino group of the third hydrolyzed compound with di-tert-butyl dicarbonate to obtain two diastereoisomers, a compound 14 and a compound 14'; wherein a specific synthesis process of the compound 14 and the compound 14' is as follows:

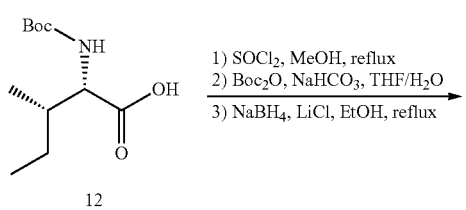

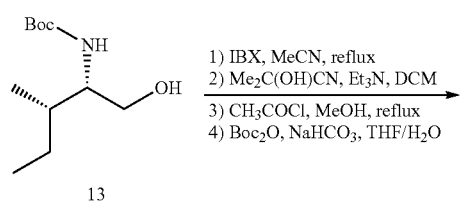

and performing a reaction on the compound 14 and pivaloyl chloride ($C_5H_9ClO$) to obtain a compound 15, removing a Boc protection group of the compound 15 with trifluoroacetic acid to obtain a sixth group-removed compound, and preforming a peptide grafting reaction on the sixth group-removed compound and a compound 16 to obtain a compound 17; and hydrolyzing a methyl ester group of the compound 17 in a reflux condition of pyridine with lithium iodide to obtain the compound 18; wherein a specific synthesis process of the compound 18 is as follows:

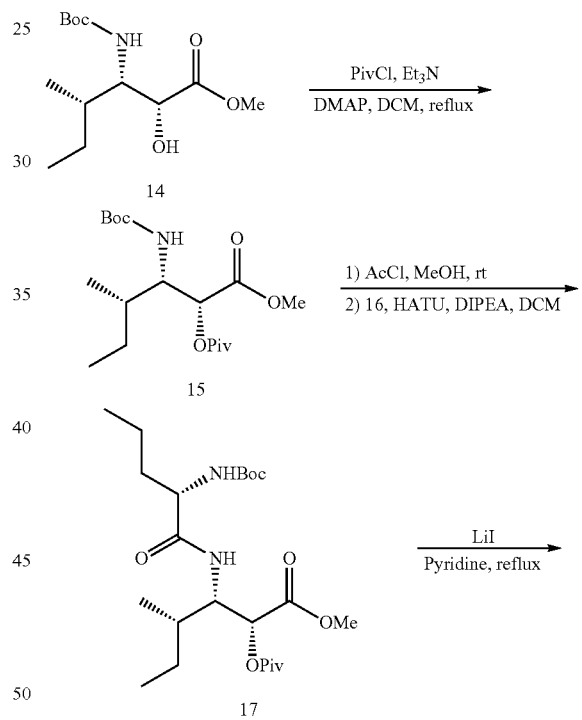

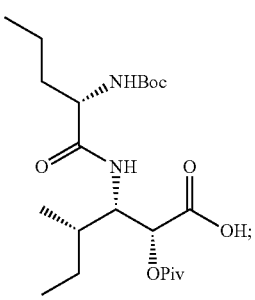

and
wherein a structure of the compound 16 is as follows:

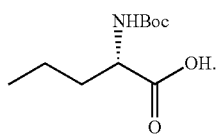
16

4. The synthesis method as claimed in claim 2, wherein a synthesis method of the compound 11 comprises:
removing a Boc protection group of a compound 8 with trifluoroacetic acid to obtain a seventh group-removed compound, and preforming a peptide grafting reaction on the seventh group-removed compound and a compound 9 to obtain a compound 10; and removing a phenoxyacetyl (Pac) protection group from the compound 10 in an acetic acid solution with zinc dust to obtain the compound 11; wherein a specific synthesis process of the compound 11 is as follows:

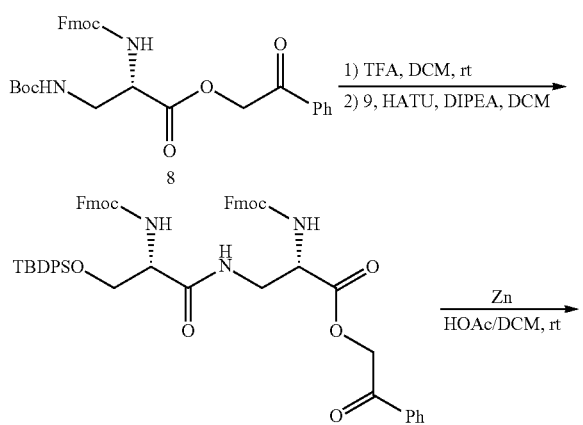

wherein a structure of the compound 9 is as follows:

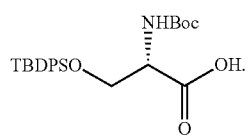
9

5. The synthesis method as claimed in claim 4, wherein a synthesis method of the compound 8 comprises:
taking a compound 6 as a starting material, protecting an amino group of the compound 6 with N-(9-fluorenyl-methoxycarbonyloxy) succinimide (Fmoc-Osu) to obtain a compound 7, and performing a Hofmann rearrangement reaction on the compound 7 to obtain a compound 3; and protecting an amino group of the compound 3 with di-tert-butyl dicarbonate, and protecting a carboxyl group of the compound 3 with phenacyl bromide (PacBr), to thereby obtain the compound 8; wherein a specific synthesis process of the compound 8 is as follows:

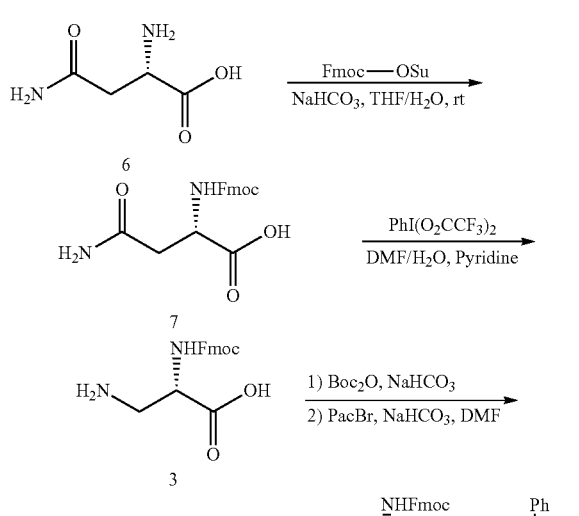

* * * * *